(12) United States Patent
Kas et al.

(10) Patent No.: US 8,697,370 B2
(45) Date of Patent: Apr. 15, 2014

(54) BIOMARKER FOR DIAGNOSIS, PREDICTION AND/OR PROGNOSIS OF SEPSIS AND USES THEREOF

(75) Inventors: Koen Kas, Schilde (BE); Griet Vanpoucke, Merelbeke (BE)

(73) Assignee: Pronota N.V., Zwijnaarde (BE)

( * ) Notice: Subject to any disclaimer, the term of this patent is extended or adjusted under 35 U.S.C. 154(b) by 407 days.

(21) Appl. No.: 12/990,841

(22) PCT Filed: May 19, 2009

(86) PCT No.: PCT/EP2009/056094
§ 371 (c)(1),
(2), (4) Date: Nov. 3, 2010

(87) PCT Pub. No.: WO2009/141359
PCT Pub. Date: Nov. 26, 2009

(65) Prior Publication Data
US 2011/0059858 A1 Mar. 10, 2011

(30) Foreign Application Priority Data
May 23, 2008 (EP) .................................. 08156837

(51) Int. Cl.
*G01N 31/00* (2006.01)
*G01N 33/53* (2006.01)
(52) U.S. Cl.
USPC ........... 435/7.21; 435/7.1; 436/501; 436/518; 530/300; 530/350; 424/130.1; 424/9.1
(58) Field of Classification Search
CPC .......... A61K 38/00; A61K 39/00; B01L 9/00; C07K 14/705; C07K 16/18; G01N 33/582; G01N 33/6893
See application file for complete search history.

(56) References Cited

U.S. PATENT DOCUMENTS

2004/0180409 A1    9/2004    McVicar et al.

FOREIGN PATENT DOCUMENTS

WO    WO 2005/071408    8/2005

OTHER PUBLICATIONS

Washington, "Aniara Grant, 2006 Coagulation Grant Winner," 15 pages, downloaded from http://www.aniara.com/Aniara-Grant/2006-Coagulation-Grant-Winner.aspx on Jul. 25, 2011.
Lu, et al. "Preparation and Characterization of monoclonal Antibody Against Protein TREM-like Transcript-1 (TLT-1)," *Hybridoma*, vol. 25, No. 1, pp. 20-26, 2006.
International Search Report dated Aug. 19, 2009 and issued to international application no. PCT/EP2009/056094.
Derive, et al. "Soluble Trem-like Transcript-1 Regulates Leukocyte Activation and Controls Microbial Sepsis," *The Journal of Immunology*, vol. 188, No. 11, pp. 5585-5592, Jun. 1, 2012.
Gattis, et al. "The Structure of the Extracellular Domain of Triggering Receptor Expressed on Myeloid Cells like Transcript-1 and Evidence for a Naturally Occurring Soluble Fragment," *The Journal of Biological Chemistry*, vol. 281, No. 19, pp. 13396-13403, May 12, 2006.
Giomarelli, et al. "Inhibition of Thrombin-induced Platelet Aggregation Using Human Single-chain Fv Antibodies Specific for TREM-like Transcript-1," *Thromb Haemost.*, vol. 97, No. 6, pp. 955-963, Jun. 2007.
Morales, et al. "Soluble TLT-1 Modulates Platelet-endothelial Cell Interactions and Actin Polymerization," *Blood Coagul Fibrinolysis*. vol. 21, No. 3, pp. 229-236, Apr. 2010.
Nurden, et al. "Phenotypic Heterogeneity in the Gray Platelet Syndrome Extends to the Expression of TREM Family Member, TLT-1," *Thromb Haemost.*, vol. 100, No. 1, pp. 45-51, Jul. 2008.
Washington, et al. "TREM-like Transcript-1 Protects Against Inflammation-associated Hemorrhage by Facilitating Platelet Aggregation in Mice and Humans," *The Journal of Clinical Investigation*, vol. 119, No. 6, pp. 1489-1501, Jun. 2009.

*Primary Examiner* — Lisa Cook
(74) *Attorney, Agent, or Firm* — Knobbe, Martens, Olson & Bear LLP

(57) ABSTRACT

Methods for the diagnosis, prognosis and prediction of sepsis in a subject using the expression levels of the biomarkers Triggering Receptor Expressed on Myeloid cells-1 (TREM-1) and TREM-like receptor transcript-1 (TLT1) as an indication of the condition of the patient, alone or in combination with further sepsis markers are disclosed. If the levels of the biomarkers indicate the presence of sepsis, the patient is treated for sepsis with an antibiotic and/or fluid resuscitation treatment.

6 Claims, 10 Drawing Sheets

BIOMARKER FOR DIAGNOSIS, PREDICTION AND/OR PROGNOSIS OF SEPSIS AND USES THEREOF

CROSS-REFERENCE TO RELATED APPLICATIONS

This application is the U.S. National Phase under 35 U.S.C. §371 of International Application PCT/EP2009/056094, filed May 19, 2009, which claims priority to EP 08156837.0, filed May 23, 2008.

FIELD OF THE INVENTION

The invention relates to protein and/or peptide based biomarkers and molecules specifically binding thereto for use in diagnosis, prognosis and prediction of disease or determination of a particular condition in a subject. In particular certain peptides or proteins as biomarkers for sepsis and methods for use of the same in diagnosis, prognosis and/or prediction of the onset of sepsis including methods involving determining increased, decreased or altered expression of said biomarkers in a sample of a subject are encompassed in the invention.

BACKGROUND TO THE INVENTION

In many diseases and conditions, a positive outcome of treatment and/or prophylaxis is strongly correlated with early and/or accurate diagnosis of the disease or condition. However, often there are no effective methods of early diagnosis and treatments are therefore often administered too late, inappropriately or to individuals who will not benefit from it. As a result, many drugs that may be beneficial for some patients may work poorly, not at all, or with adverse effect in other patients. Thus, there is a need for innovative strategies that will allow early detection, prediction, prognosis, diagnosis and treatment of diseases and other biological conditions. There is also a need to determine the ability, or inability, of a patient to tolerate medications or treatments.

Sepsis is more commonly called a blood stream infection or blood poisoning. It is the presence of bacteria (bacteraemia), infectious organisms, or their toxins in the blood or other tissues of the body. Sepsis often occurs in patients suffering from systemic inflammatory response syndrome (SIRS), as a result of e.g. surgery, trauma, burns, pancreatitis and other non-infectious events that cause inflammation to occur. SIRS combined with an infection is called sepsis and can occur in many different stages of severity. The infection can occur simultaneously with the occurrence of SIRS e.g. due to infection of a wound or trauma or can occur later due to the latent presence of an infectious organism. Sepsis may be associated with clinical symptoms of systemic (body wide) illness, such as fever, chills, malaise, low blood pressure, and mental status changes. Sepsis can be a serious situation, an often life threatening disease calling for urgent and comprehensive care. Treatment depends on the type of infection, but usually begins with antibiotics or similar medications.

As sepsis may be the result of infection by a wide variety of organisms it is a condition which is particularly difficult to predict and diagnose early enough for effective intervention. It is an excessive and uncontrolled inflammatory response in an individual usually resulting from an individual's inappropriate immune system response to a pathogenic organism. Moreover, there may not be significant numbers of organisms at accessible sites or in body fluids of the affected individual, thus increasing the difficulty of diagnosis. There is therefore a need to identify biomarkers indicating the risk, or early onset of sepsis, regardless of the causative agent, to allow early and effective intervention. Differentiating between patients who are at risk of developing sepsis and those who are not, will also assist in managing the disease condition. In particular, the ability to distinguish SIRS from sepsis in a patient is highly desirable, e.g. in a clinical setting for patients undergoing surgery or transplantation, suffering from trauma, etc which have to be monitored during and/or after their stay in the hospital.

There is therefore an immediate need for the identification of biomarkers that are measurable and specific for the condition, and indicative of the risk of progression to, or early onset of, sepsis as well as methods for using said markers in screening.

Biomarkers are biological indicators that signal a changed physiological state due to a disease or therapeutic intervention. It has been demonstrated that certain substances, including proteins and peptides, are expressed differentially in diseased tissue and bodily fluid samples in certain conditions such as sepsis, when compared to normal tissue and bodily fluid samples. Hence, differentially expressed protein/peptides(s) present in (or absent from) diseased samples from a patient, whilst being absent (or present) in normal tissue, is/are candidate biomarkers for that disease or condition.

Often a single biomarker alone may be insufficient for the accurate diagnosis of a disease or condition, especially one as complex as sepsis. As a result there is a continuing need for identification of biomarkers that may be used to identify or profile the condition at various stages in its pathology.

The only FDA-approved diagnostic biomarker for distinguishing sepsis from non-infectious causes of systemic inflammatory response syndromes (SIRS) currently available is Procalcitonin (PCT). The diagnostic and prognostic performance of PCT is however rather low as was shown in a recent report of Tang and co-workers (Tang B. M. J. et al., The Lancet vol 7:p 210-217, 2007), indicating that the procalcitonin test cannot accurately distinguish sepsis from SIRS in critically ill adult patients.

C-reactive protein is a further widely used marker for diagnosing sepsis, but is unable to distinguish between sepsis and SIRS without infection.

The inventors have now developed methods that enable rapid quantification, qualification and comparison of protein and peptide profiles derived from different biological samples and as a result have identified novel biomarkers for diagnosis, prognosis and/or prediction of sepsis and its different stages.

SUMMARY OF THE INVENTION

The present invention provides new biomarkers for sepsis that enable the medical doctor or the clinician of more accurate prediction, prognosis and diagnosis of SIRS (systemic inflammatory response syndrome), sepsis, severe sepsis or MODS (multiple organ dysfunction score) or that can differentiate between said different conditions and methods for accurate, rapid, and sensitive prediction, prognosis and/or diagnosis of said different conditions through (1) a measurement of the quantity or quality of one or more of said biomarkers taken from a biological sample from a reference subject, be it a healthy subject or a patient having SIRS, sepsis, severe sepsis or MODS to provide a "reference biomarker profile" for said biomarkers that is indicative of the respective condition and (2) through comparison of this reference biomarker profile with a "candidate biomarker profile" of said biomarker(s) from a comparable biological sample from a subject that has SIRS, sepsis, severe sepsis or MODS or is at risk of developing any of these conditions or is at a particular stage in the progression of sepsis.

A "reference biomarker profile" may be obtained from a population of individuals who (1) do not have and have never had sepsis, (2) who have sepsis or are suffering from the onset of sepsis or a particular stage in the progression of sepsis or (3) who have SIRS without infection. If the biomarker profile from the test subject contains characteristic features of the biomarker profile from the reference population, then the individual can be diagnosed as respectively being (1) healthy, (2) being at risk of developing sepsis, having sepsis or as being at the particular stage in the progression of sepsis or (3) as having SIRS. The reference biomarker profile may also be obtained from various populations of individuals including those who are suffering from SIRS or those who are suffering from an infection but who are not suffering from SIRS. Accordingly, the present invention allows the clinician to distinguish between those patients who have SIRS but are not likely to develop severe sepsis, who have sepsis, or who are at risk of developing sepsis.

In one aspect of the invention there is provided a method for the prediction, prognosis and/or diagnosis of sepsis or of the differentiation between SIRS and sepsis in a subject comprising obtaining a candidate biomarker profile from a biological sample taken from said subject wherein said candidate biomarker profile is based on the measurement of the quantity of TREM-like-transcript-1 (TLT-1/TREML1), one of the biomarkers identified in the present invention, in said sample, and comparing said candidate biomarker profile with a reference biomarker profile obtained form a healthy subject or a patient having SIRS.

Also provided by the invention is a method for the prediction, prognosis and/or diagnosis of sepsis or the differentiation between SIRS and sepsis in a subject comprising: obtaining a candidate biomarker profile from a biological sample taken from said subject wherein said candidate biomarker profile is based on at least one or two biomarkers selected from the group consisting of TREM-like-transcript-1 (TLT-1/TREML1), NGAL, TREM-1, Procalcitonin (PCT) and c-Reactive Protein (CRP) and comparing said candidate profile with a reference biomarker profile obtained form a healthy subject or a patient having SIRS.

The invention further provides for a method for prediction, prognosis and/or diagnosis of sepsis or the differentiation between SIRS and sepsis in a subject comprising measuring the level of at least one or two biomarkers selected from the group consisting of TREM-like-transcript-1 (TLT-1/TREML1), NGAL, TREM-1, Procalcitonin (PCT) and c-Reactive Protein (CRP) in a biological sample from said subject, using said obtained measurements to create a profile for said biomarkers, and comparing said profile with a reference biomarker profile obtained form a healthy subject or a patient having SIRS.

In a further embodiment, the invention provides for a method for the diagnosis, prognosis and/or prediction of sepsis or distinguishing between SIRS and sepsis in a subject comprising determining a quantity of at least one or two biomarkers selected from the group consisting of TREM-like-transcript-1 (TLT-1/TREML1), NGAL, TREM-1, Procalcitonin (PCT) and c-Reactive Protein (CRP) in a sample obtained from a subject; and comparing the quantity of the selected biomarkers in the test subject sample with a range of normal values of the selected biomarkers in control subjects; whereby an increase or decrease in the quantity of the selected biomarker in the sample to a level higher or lower than the range of normal values of the selected biomarkers is indicative of sepsis.

In a further aspect the invention provides for a method for the diagnosis, prognosis and/or prediction of sepsis or distinguishing between SIRS and sepsis in a subject comprising determining a quantity of at least one or two biomarkers selected from the group consisting of TREM-like-transcript-1 (TLT-1/TREML1), NGAL, TREM-1, Procalcitonin (PCT) and c-Reactive Protein (CRP) and comparing the quantity of the selected biomarkers in the test subject sample with a range of values of the selected biomarkers obtained from subjects with sepsis; whereby a comparable quantity of the selected biomarkers in said sample to the range of values of the selected biomarkers in subjects with sepsis is indicative of sepsis.

Alternatively, the invention provides for a method for the prediction, prognosis and/or diagnosis of sepsis or the differentiation between SIRS and sepsis in a subject comprising obtaining a candidate antibody profile from a biological sample taken from said individual wherein said candidate antibody profile is based on an antibody to at least one or two biomarkers selected from the group consisting of TREM-like-transcript-1 (TLT-1/TREML1), NGAL, TREM-1, Procalcitonin (PCT) and c-Reactive Protein (CRP) and comparing said candidate antibody profile with a reference antibody profile.

In a further embodiment, the invention provides for a method for determining whether a subject is responsive to treatment for sepsis with a substance, comprising the steps of obtaining a candidate biomarker profile from a biological sample taken from said individual wherein said candidate biomarker profile is based on at least one or two biomarkers selected from the group consisting of TREM-like-transcript-1 (TLT-1/TREML1), NGAL, TREM-1, Procalcitonin (PCT) and c-Reactive Protein (CRP) and comparing said candidate profile with a reference biomarker profile.

In a preferred embodiment, one of the selected biomarkers for use in the methods of the invention is selected from the group consisting of TREM-like-transcript-1 (TLT-1/TREML1).

In yet a further embodiment, the selected biomarkers for use in the methods of the invention are selected from the group consisting of TREM-like-transcript-1 (TLT-1/TREML1) and TREM-1, alone or in combination with PCT, NGAL or CRP, preferably PCT.

In another preferred embodiment, the combination of biomarkers for use in the methods of the invention is the combination of the markers TREM-like-transcript-1 (TLT-1/TREML1), NGAL, TREM-1, Procalcitonin (PCT) and C-reactive protein (CRP).

Preferred samples to be analysed in the methods of the present invention are blood or urine, more preferable the sample is serum or plasma, most preferably serum.

In a preferred embodiment, the method of the invention uses immunoassay technology selected from the group of direct ELISA, indirect ELISA, sandwich ELISA, competitive ELISA, multiplex ELISA, radioimmunoassay, or ELISPOT technologies to establish the biomarker profile. In alternative embodiment, the biomarker profile is established using mass spectrometry analysis methods of the proteins present in said sample.

A further object of the invention is a kit for the prediction, prognosis and/or diagnosis of sepsis comprising binding molecules to at least one or two biomarkers selected from the group consisting of TREM-like-transcript-1 (TLT-1/TREML1), NGAL, TREM-1, Procalcitonin (PCT) and C-reactive protein (CRP). Such a kit may further comprise a biomarker reference profile or a reference value of the quantity of one or more biomarkers from the invention, obtained from a healthy subject or a subject having SIRS for comparison of the results.

In a preferred embodiment, the kit of the invention comprises at least binding molecules that are specific for binding biomarkers selected from the group consisting of TREM-like-transcript-1 (TLT-1/TREML1), NGAL, TREM-1, Procalcitonin (PCT) and C-reactive protein (CRP). In an alternative embodiment, such a kit further comprises binding molecules specific for any of the other biomarkers of the invention or with any other known marker for sepsis, for detecting sepsis or SIRS.

In a preferred embodiment, the kit of the invention comprises binding molecules that are specific for binding TREM-like-transcript-1 (TLT-1/TREML1) and TREM-1. In a further embodiment, the kit comprises binding molecules that are specific for binding TREM-like-transcript-1 (TLT-1/TREML1), NGAL, TREM-1, Procalcitonin (PCT) and C-reactive protein (CRP).

In a preferred embodiment, the kit of the invention comprises binding molecules that are specific for TREM-like-transcript-1 (TLT-1/TREML1), alone or in combination with PCT, NGAL or CRP, preferably PCT.

In yet a further embodiment, the kit of the invention comprises binding molecules that are specific for binding the biomarkers selected from the group consisting of: TREM-like-transcript-1 (TLT-1/TREML1) and TREM-1, alone or in combination with PCT.

In another preferred embodiment, the kit of the invention comprises binding molecules that are specific for binding the biomarkers TREM-like-transcript-1 (TLT-1/TREML1), NGAL, TREM-1, Procalcitonin (PCT) and C-reactive protein (CRP).

Preferred binding molecules of the invention are monoclonal antibodies, polyclonal antibodies, aptamers, photoaptamers, specific interacting proteins, and specific interacting small molecules.

In a further embodiment, the invention encompasses a protein microarray comprising protein fragments of at least two biomarkers selected form the group consisting of TREM-like-transcript-1 (TLT-1/TREML1), NGAL, TREM-1, Procalcitonin (PCT) and C-reactive protein (CRP) coated on a solid phase.

Methods of the invention further comprise methods in which measurements of any combination of the biomarkers selected from the group consisting of TREM-like-transcript-1 (TLT-1/TREML1), NGAL, TREM-1, Procalcitonin (PCT) and C-reactive protein (CRP) are included in the creation of the candidate and reference profile. It will be understood that additional biomarkers may also be included such as biomarkers already used for the diagnosis or prognosis of sepsis or SIRS.

The invention further provides methods as outlined above wherein the profile is created using antibodies to said biomarkers. In this case the candidate and reference biomarker profiles will be created based on measurements of antibodies to the biomarkers and are referred to hereinafter as candidate antibody profiles and reference antibody profiles.

Figure 1:
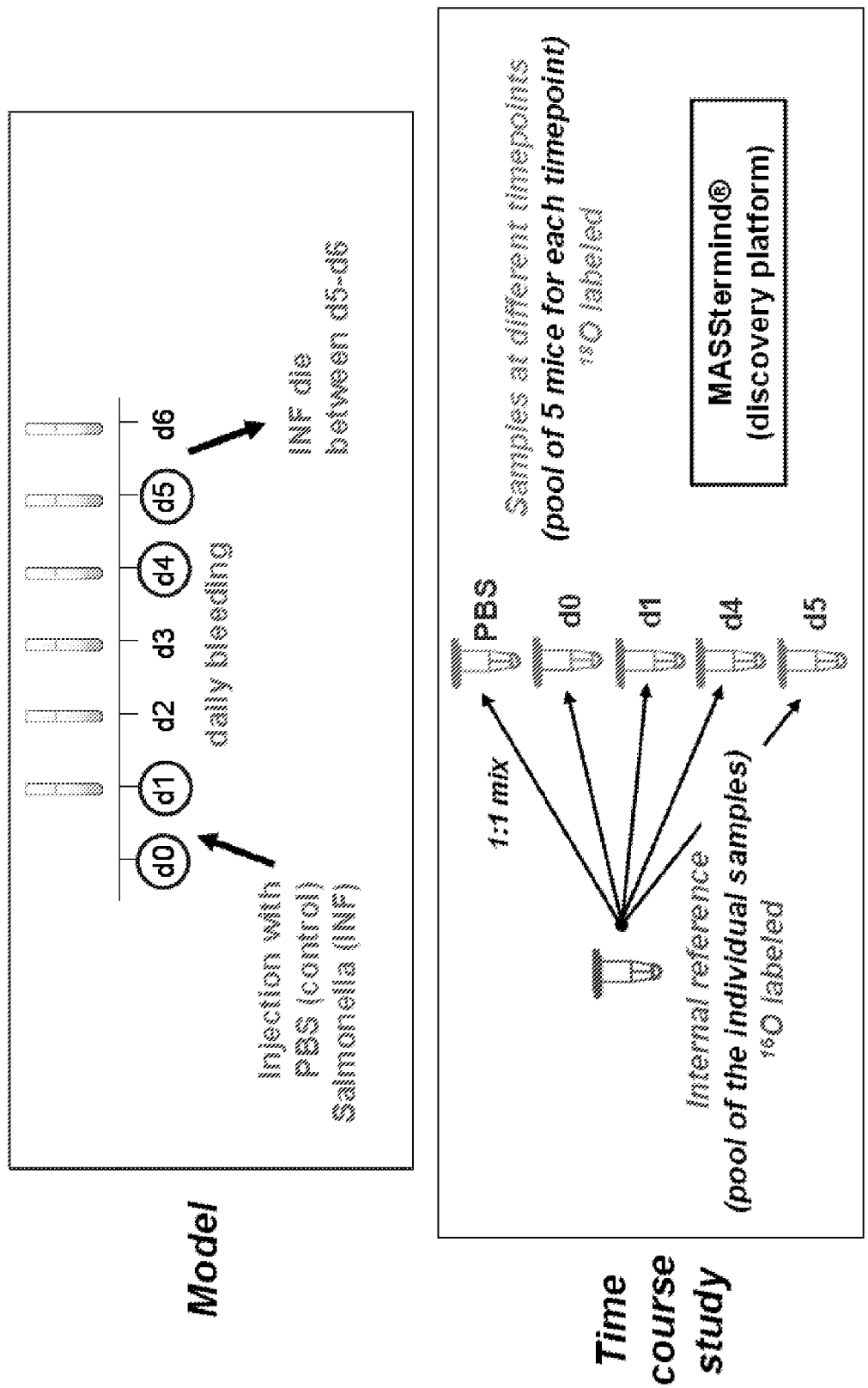
FIG. 1: A schematic overview of the mouse Sepsis model used for the identification of new biomarkers for sepsis. In short, mice are infected with Salmonella on day 0 (INF) or are injected with PBS (Control) and are followed during 7 consecutive days or until they die. Most mice infected with Salmonella die between five and seven days after infection. Further detail is given on the experimental set-up of the time course study: samples taken at 5 different points are all compared to an internal reference using the MASStermind™ discovery platform
Figure 2:
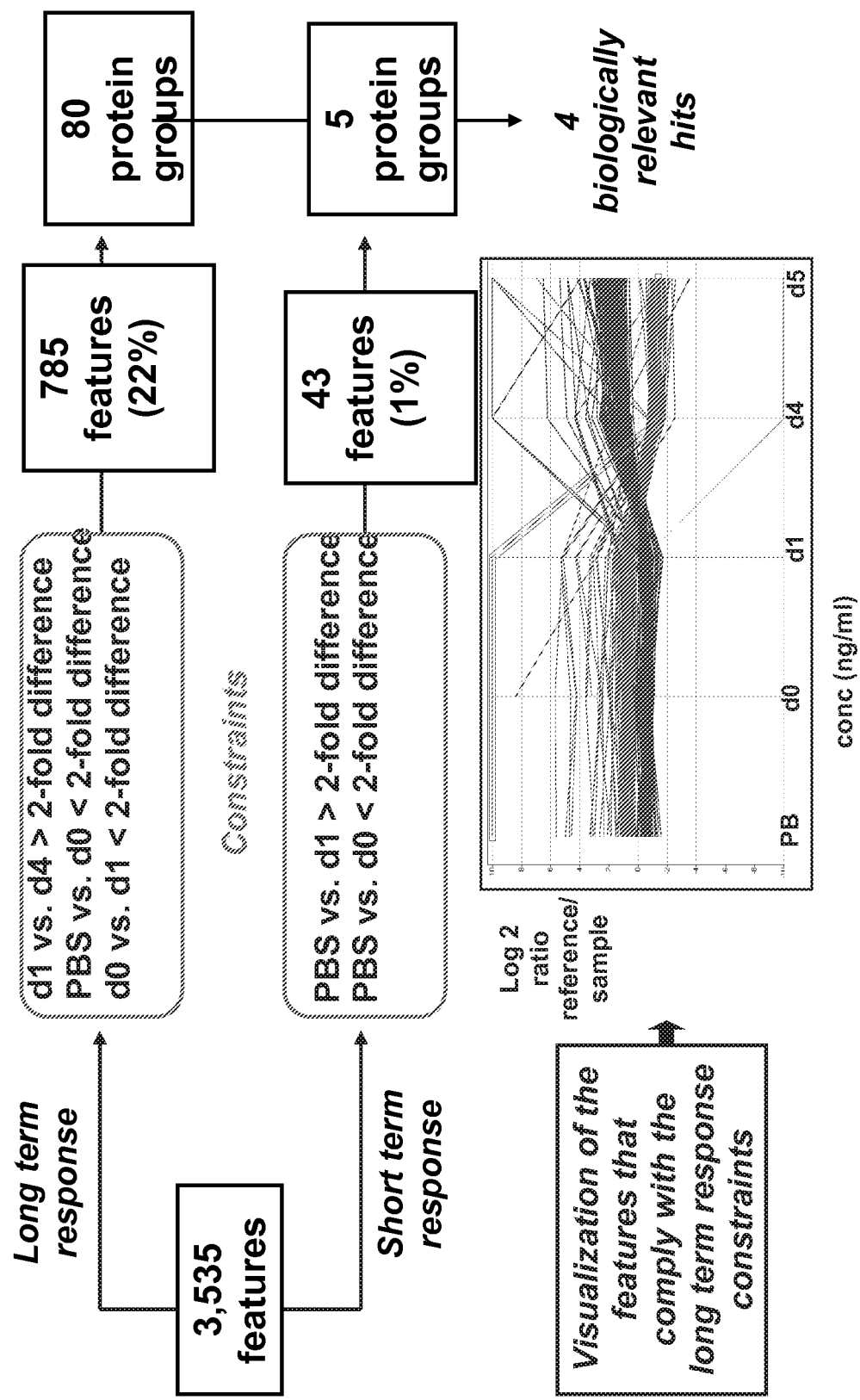
FIG. 2: Schematic representation of the analysis of the test results of the Cofradic™ procedure, illustrating the constraints used to select features with long term vs. short term response and the number of proteins identified for each. Four of these potential biomarkers were selected for further investigation in view of their biological relevance.
Figure 3:
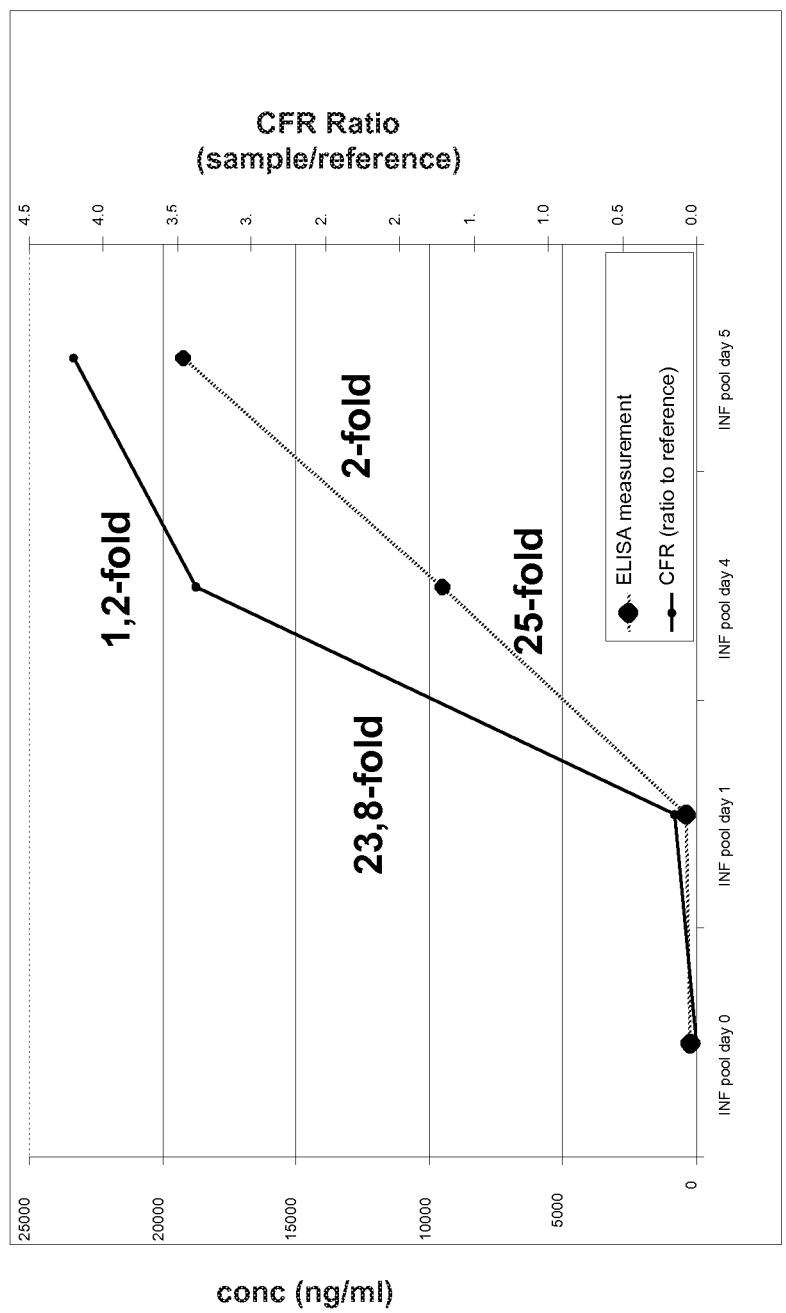
FIG. 3: Schematic representation of the change in expression levels of one of the candidate biomarkers for sepsis, NGAL as measured using Cofradic™ and ELISA. ELISA measurement (graph with large squares) using an anti-mouse NGAL antibody on the same samples used in the Cofradic™ analysis, compared to the Cofradic™ test results (graph with small circles). As can be seen from this graph, the Cofradic™ results are confirmed by the ELISA results and both show a clear up-regulation of the NGAL expression in sepsis versus control mice, starting already early in the process.
Figure 4:
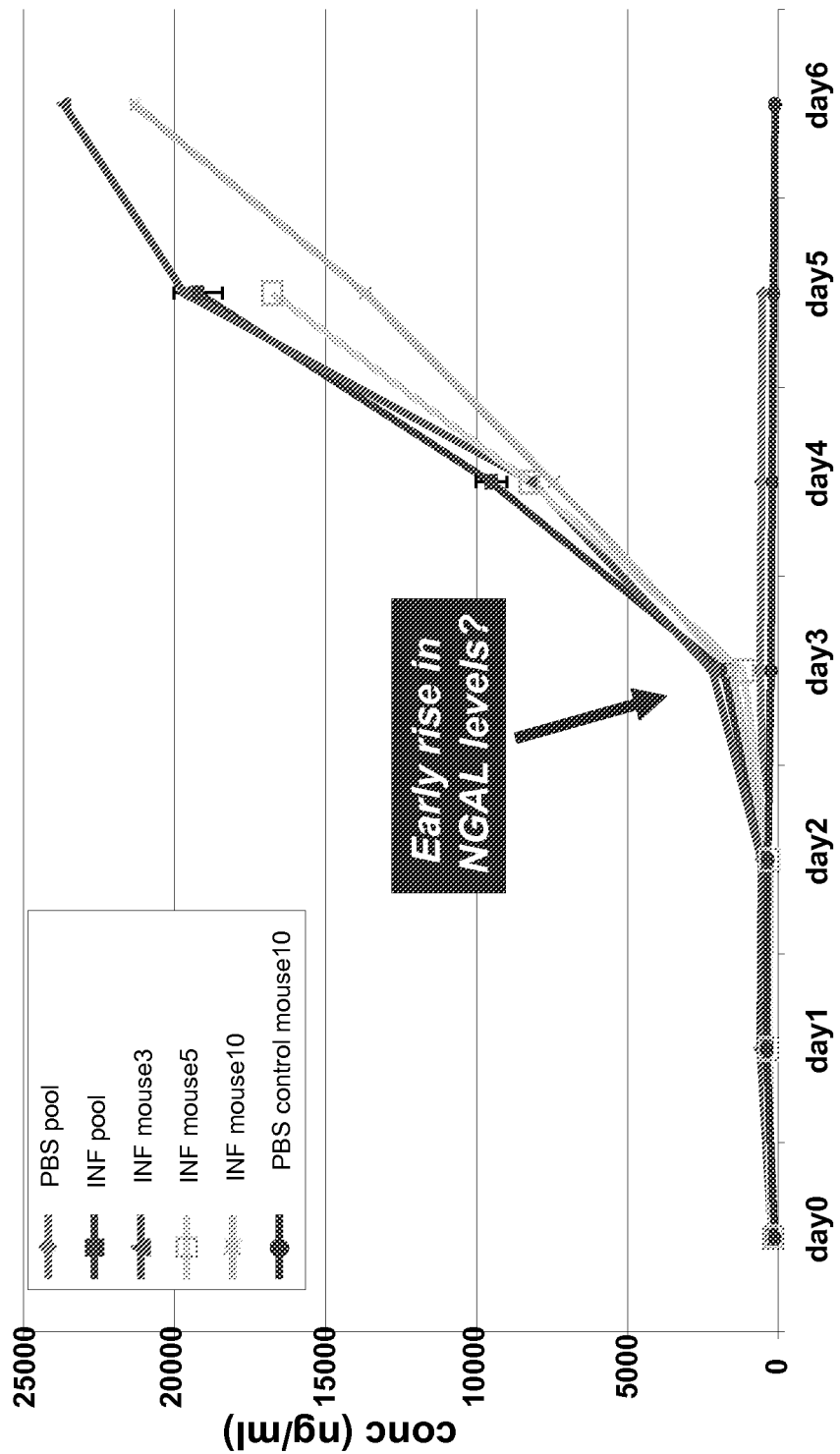
FIG. 4: Representation of NGAL-ELISA test results on pooled mouse samples and individual mouse samples in order to determine the representability of the experimental set-up. As can be seen from the figure, the individual samples (INF mouse #) all show a very similar increase in NGAL protein expression during sepsis progression, corresponding to the graph of the pooled sample (INF pool).

It is clear from the figure that TLT-1 expression is reduced in lanes 2-4 (septic subjects), when compared to lane 1 (healthy subject).

DETAILED DESCRIPTION OF THE INVENTION

Sepsis may be characterised as an initial systemic inflammatory response syndrome (SIRS), sepsis, severe sepsis (sepsis with acute organ dysfunction), septic shock (sepsis with refractory arterial hypotension), multiple organ dysfunction or failure and death.

"SIRS" is a systemic inflammatory response syndrome with no signs of infection. It can be characterized by the presence of at least two of the four following clinical criteria: fever or hypothermia (temperature 100.4° F. [38° C.] or 96.8° F. [36° C.]), tachycardia (90 beats per minute), tachypnea (20 breaths per minute or PaCO2 4.3 kPa [32 mm Hg] or the need for mechanical ventilation), and an altered white blood cell count of 12,000 cells/mL, 4000 cells/mL, or the presence of 10% band forms, respectively.

"Sepsis" can generally be defined as SIRS with an infection. Infection can be diagnosed by standard textbook criteria or, in case of uncertainty, by an infectious disease specialist.

"Severe sepsis" can be defined as the presence of sepsis and at least one of the following manifestations of inadequate organ perfusion or function: hypoxemia (PaO2 10 kPa [75 mm Hg]), metabolic acidosis (pH 7.30), oliguria (output 30 mL/hr), lactic acidosis (serum lactate level 2 mmol/L), or an acute alteration in mental status without sedation (i.e., a reduction by at least 3 points from baseline value in the Glasgow Coma Score).

"Septic shock" can be defined as the presence of sepsis accompanied by a sustained decrease in systolic blood pressure (90 mm Hg, or a drop of 40 mm Hg from baseline systolic blood pressure) despite fluid resuscitation, and the need for vasoactive amines to maintain adequate blood pressure.

As many organisms can be the cause of sepsis, diagnosis often takes time and requires testing against panels of possible agents. Sepsis can also arise in many different circumstances and therefore sepsis can be further classified for example in: incarcerated sepsis which is an infection that is latent after the primary lesion has apparently healed but may be activated by a slight trauma; catheter sepsis which is sepsis occurring as a complication of intravenous catheterization; oral sepsis which is a disease condition in the mouth or adjacent parts which may affect the general health through the dissemination of toxins; puerperal sepsis which is infection of the female genital tract following childbirth, abortion, or miscarriage; or sepsis lenta, which is a condition produced by infection with a-hemolytic streptococci, characterized by a febrile illness with endocarditis.

For the purposes of this invention, the wording "sepsis" is used hereafter to include all conditions and stages of the disease progression.

According to the present invention, sepsis may be predicted or diagnosed by obtaining a profile of biomarkers from a sample obtained from an individual. The present invention is particularly useful in predicting and diagnosing sepsis in an individual who has an infection, or has sepsis, but who has not yet been diagnosed as having sepsis, who is suspected of having sepsis, or who is at risk of developing sepsis. The present invention may also be used to differentiate between SIRS and sepsis and to detect and diagnose SIRS in an individual or to detect that a person is not at risk of developing sepsis. The present invention also may be used to detect various stages of the sepsis progression such as sepsis, severe sepsis, septic shock, and organ failure.

Biomarker profiles may be created in a number of ways and may be a ratio of two or more measurable aspects of a biomarker. A biomarker profile comprises at least two measurements, where the measurements can correspond to the same or different biomarkers. A biomarker profile may also comprise at least three, four, five, 10, 20, 30 or more measurements. In one embodiment, a biomarker profile comprises hundreds, or even thousands, of measurements.

The profile of a biomarkers obtained from an individual namely the candidate biomarker profile, is compared to a reference biomarker profile. The reference biomarker profile can be generated from one individual or a population of individuals. The population, for example, may comprise two, ten, or many more, possibly hundreds of individuals.

The reference biomarker profile and the candidate biomarker profiles that are compared in the methods of the present invention may be generated from the same individual for the purpose of monitoring disease progression. In this instance it would be expected that the candidate and reference profiles are generated from biological samples taken at different time points and compared to one another. Such a comparison may be used, for example, to determine the status of sepsis in the individual by repeated measurements over time.

The reference biomarker profiles may be chosen from individuals who are sepsis-positive and suffering from one of the stages in the progression of sepsis, or from individuals with increased risk of developing sepsis, or from populations of individuals who do not have SIRS, from individuals who do not have SIRS but who are suffering from an infectious process, from individuals who are suffering from SIRS without the presence of sepsis or from individuals who are suffering from the onset of sepsis. The reference biomarker profile may be generated from a healthy population.

The methods of the present invention comprise comparing a candidate biomarker profile with a reference biomarker profile. As used herein, comparison includes any means to determine at least one difference in the candidate and the reference biomarker profiles. A comparison may include a visual inspection, an arithmetical or statistical comparison of measurements. Such statistical comparisons include, but are not limited to, applying a rule. If the biomarker profiles comprise at least one standard, the comparison to determine a difference in the biomarker profiles may also include measurements of these standards, such that measurements of the biomarker are correlated to measurements of the internal standards. The comparison should enable prognosis, diagnosis and/or predication of the presence of sepsis, of increased risk of sepsis, of SIRS or even absence of sepsis or SIRS. Alternatively, the comparison can indicate the stage of sepsis at which an individual may be.

The present invention is based on the identification of new biomarkers of sepsis. However, these may be used in conjunction with other biomarkers and these may include any biological compound such as a protein or fragment thereof, a peptide, a polypeptide, a proteoglycan, a glycoprotein, a lipoprotein, a carbohydrate, a lipid, a nucleic acid, or other polymer, or any biological molecule that is present in the biological sample and that may be isolated from, or measured in, the biological sample. Furthermore, a biomarker can be the entire molecule, or it can be part thereof that may be partially functional or recognized, for example, by an antibody, aptamer or other specific binding molecule. A biomarker is useful if it is specific for sepsis and measurable. Such a measurable aspect may include, for example, the presence, absence, or concentration of the biomarker in the biological sample from the individual and/or its presence as part of a profile of biomarkers.

Biomarkers Identified in the Present Invention

As is clear from the examples below, we analysed blood samples from a mouse model of sepsis at different time points before and after infection with a Salmonella strain. The time course study was run in reference design mode on Pronota's MASStermind™ discovery platform, using the well known Cofradic™ procedure. In a reference design study each sample is measured against a reference sample, typically a pool of all patient samples. For each feature present in a certain sample a ratio is obtained which represents the fold difference of the feature intensity in the reference versus feature intensity in the sample. Combining all feature data from all samples into an expression matrix allows comparing features intensities between samples and between groups of samples.

All serum samples were depleted for the most abundant proteins (e.g. albumin, transferring, IgG, etc.) using an Agilent column. Depletion efficiency was checked using ELISAs and Western Blot analysis. The reference pool was prepared at this stage and this reference was considered as a normal sample for the rest of process. Samples were prepared for MASStermind™ analysis according to the standard N-ter COFRADIC™ procedures. Reference pool and samples were differentially labelled by trypsin mediated incorporation of $^{18}$O/$^{16}$O, where the different samples carried the heavy oxygen label and the reference the $^{16}$O. Just before COFRADIC™ sorting each sample was mixed with the reference at equal protein masses. After sorting and NanoLC, separations MS spectra were obtained. MS data were de-isotoped, clustered and features were constructed using in house developed software called euCatLabel. The output of this data processing is an expression matrix containing all features from all analyzed samples. Each feature is represented by a unique combination of m/z, COFRADIC™ sorting pool and NanoLC retention time and features can be present in a number of samples ranging from 1 to all. If a feature is present in a sample it will carry a ratio, which represents intensity of the feature in the reference sample (i.e. the $^{16}$O peak) over the intensity in the respective sample (the $^{18}$O peak). Recurrent quantifiable features are features with a reliable ratio reading in at least two samples.

Using this approach, we identified 2 biomarkers that showed a change in expression during the course of infection and sepsis development in this mouse model. In order to assess the use of these biomarkers in the diagnosis of sepsis in humans and in the differentiation between SIRS and sepsis, ELISA measurements were performed and the data were used to assess the power of the biomarkers or combinations thereof in differentiating subjects being either SIRS or sepsis.

Neutrophil Gelatinase-Associated Lipocalin (NGAL/Lipocalin-2 Lcn-2)

Neutrophil gelatinase-associated lipocalin (NGAL) is a 21-kD protein of the lipocalin super family. Lipocalins comprise a class of proteins that are characterized by eight β-strands that form a β-barrel defining a calyx. The calyx binds and transports low molecular weight molecules, which are thought to define the biologic activity of the lipocalin. The ligand of NGAL was discovered on the basis of the observation that recombinant NGAL, when expressed in bacteria, appeared either colourless or light rose, depending on the bacterial strain used for expression of the protein. This colour was found to be related to the presence of iron and a small iron-binding molecule called enterochelin (or its degradation product, 2,3-dihydroxybenzoic acid), which is produced by some strains of bacteria. Bacteria produce siderophores to scavenge iron from the extracellular space and use specific transporters to recover the siderophore:iron complex, ensuring their iron supply. Accordingly, NGAL prevented growth of the bacterial strains that rely on the production of enterochelin to satisfy their iron demands. The biologic significance of this finding was demonstrated in genetically modified mice, which are deficient for both copies of the NGAL gene. These animals were more sensitive to certain Gram-negative bacteria and more readily died of sepsis than did wild-type mice. Therefore, NGAL comprises a critical component of innate immunity to bacterial infection. NGAL seems to have more complex activities than its antimicrobial effect. The expression of NGAL rises 1000-fold in humans and rodents in response to renal tubular injury, and it appears so rapidly in the urine and serum that it is useful as an early biomarker of renal failure. Induction of NGAL may limit tubular injury, an effect that may be independent from its bacteriostatic actions. In fact, mounting evidence points toward growth factor effects of NGAL that modulate various cellular responses, such as proliferation, apoptosis, and differentiation, but this is not well understood mechanistically. Some of these effects, however, are enhanced when NGAL is associated with siderophores and iron, raising the possibility that in the absence of bacterial infection, endogenous molecules associate with NGAL to mediate its iron-binding properties (for a review cf. Schmitt-Ott et al., 2007, J. Am. Soc. Neprol. vol. 19:407-413). NGAL has recently been implicated in diagnosis of sepsis as can be seen from international patent application WO 2007/041623 A2 held by Biosite Inc, where it is part of a panel of biomarkers of sepsis together with MIP3 and CRP.

TREM-Like-Transcript-1 (TREML1/TLT1)

TREML1 is a transmembrane receptor, specifically found to be expressed on platelets. It has for this reason been implicated in platelet aggregation. The TREML1 receptor can be present in two forms, a membrane bound full-length protein of 30 kDa and a secreted soluble variant, lacking the transmembrane region and having a weight of 20 kDa. The soluble form can easily be detected in blood or serum samples, whereas the membrane bound form is not detected in blood or serum samples, but only in platelets themselves as shown in the examples below.

TREM-1 (Triggering Receptor Expressed on Myeloid Cells-1)

The triggering receptor expressed on myeloid cells 1 (TREM-1) plays an important role in the innate immune response related to severe infections and sepsis. Modulation of TREM-1-associated activation improves the outcome in rodent models for pneumonia and sepsis. However, the identity and occurrence of the natural TREM-1 ligands are so far unknown, impairing the further understanding of the biology of this receptor. A ligand for TREM-1 on human platelets was previously reported. Using a recombinant TREM-1 fusion protein, specific binding of TREM-1 to platelets was demonstrated. TREM-1-specific signals are required for the platelet-induced augmentation of polymorphonuclear leukocyte (PMN) effector functions (provoked by LPS). However, TREM-1 interaction with its ligand is not required for platelet/PMN complex formation, which is dependent on integrins and selectins. Taken together, the results indicate that the TREM-1 ligand is expressed by platelets, and the TREM-1/ligand interaction contributes to the amplification of LPS-induced PMN activation (Haselmayer et al., 2007 Blood vol. 110(3):1029-35). TREM-1 has been previously identified as a possible marker for sepsis prognosis and is up-regulated in patients with SIRS or sepsis as compared to healthy subjects. A plasma soluble TREM-1 level higher than 60 ng/ml was seen as indicative of SIRS or sepsis (Gibot et al., 2004, Annals 2004 141: 9-15).

The combined measurement of serum PCT and bronchoalveolar lavage (BAL) sTREM-1 concentrations has been reported to be of interest in detecting the presence of a nosocomial sepsis and in discriminating Ventilator-Associated Pneumonia (VAP) versus extrapulmonary infection by Gibot et al., 2007 (Scand J Infect Dis. 39(6-7):604-8). Tejera A et al., 2007, (Cytokine 38(3):117-23) in addition reported on the usefulness of detecting TREM-1 protein levels in serum for prognosing sepsis.

Procalcitonin (PCT)

The known sepsis biomarker Procalcitonin (PCT) is a precursor of the hormone calcitonin, which is involved with calcium homeostasis, and is produced by the C-cells of the thyroid gland. It is there that procalcitonin is cleaved into calcitonin, katacalcin and a protein residue. It is not released into the blood stream of healthy individuals. With the derangements that a severe infection with an associated systemic response brings, the blood levels of procalcitonin may rise to 100 ng/ml. In blood serum, procalcitonin has a half-life of 25 to 30 hours. Measurement of procalcitonin can be used as a marker of severe sepsis and generally grades well with the degree of sepsis, although levels of procalcitonin in the blood are very low. PCT has the greatest sensitivity (85%) and specificity (91%) for differentiating patients with SIRS from those with sepsis, when compared with IL-2, IL-6, IL-8, CRP and TNF-alpha. However, the test is not routinely used and has yet to gain widespread acceptance (cf. Meisner et al., 1999, Crit Care vol 3(1):45-50).

C-Reactive Protein (CRP)

Another known sepsis biomarker is C-reactive protein (CRP), which is a plasma protein, an acute phase protein produced by the liver and by adipocytes. It is a member of the pentraxin family of proteins and has been widely used as a marker for sepsis, especially in neonates. Its accuracy is however controversial.

Any of the above markers identified in the present invention can be used separately or in combination in the kits, microarrays and methods of the invention. Any combination of two or more of the markers identified in this invention can be used together. In addition, any combination of one or more of the newly identified biomarkers can be used together with other known sepsis markers. One preferred known sepsis marker is the (soluble) TREM-1 marker, the PCT (procalcitonin) marker or the CRP (c-reactive protein) marker.

Preferred combinations of the markers are combinations of TREML-1 and TREM-1, wherein an up regulation of TREM-1 and a down-regulation of TREML-1 is indicative of sepsis in the subject.

In a preferred embodiment, the combination always comprises the TREML-1 and TREM-1 biomarkers, alone or in combination with any one or more other biomarkers of sepsis or SIRS selected from the group consisting of CRP, PCT or NGAL.

In an even more preferred embodiment, the combination always comprises the TREML-1 biomarker, alone or in combination with any one or more other biomarkers of sepsis or SIRS selected from the group consisting of CRP, PCT or NGAL.

Generation of Biomarker Profiles

Biomarker profiles may be generated by the use of one or more separation methods. For example, suitable separation methods may include a mass spectrometry method, such as electrospray ionization mass spectrometry (ESI-MS), ESI-MS/MS, ESI-MS/(MS)$^n$ (n is an integer greater than zero), matrix-assisted laser desorption ionization time-of-flight mass spectrometry (MALDI-TOF-MS), surface-enhanced laser desorption/ionization time-of-flight mass spectrometry (SELDI-TOF-MS), desorption/ionization on silicon (DIOS), secondary ion mass spectrometry (SIMS), quadrupole time-of-flight (Q-TOF), atmospheric pressure chemical ionization mass spectrometry (APCI-MS), APCI-MS/MS, APCI-(MS)$^n$, atmospheric pressure photoionization mass spectrometry (APPI-MS), APPI-MS/MS, and APPI-(MS)$^n$. Other mass spectrometry methods may include, inter alia, quadrupole, fourier transform mass spectrometry (FTMS) and ion trap. Other suitable separation methods may include chemical extraction partitioning, column chromatography, ion exchange chromatography, hydrophobic (reverse phase) liquid chromatography, isoelectric focusing, one-dimensional polyacrylamide gel electrophoresis (PAGE), two-dimensional polyacrylamide gel electrophoresis (2D-PAGE) or other chromatography, such as thin-layer, gas or liquid chromatography, or any combination thereof. In one embodiment, the biological sample may be fractionated prior to application of the separation method.

Biomarker profiles may also be generated by methods that do not require physical separation of the biomarkers themselves. For example, nuclear magnetic resonance (NMR) spectroscopy may be used to resolve a profile of biomarkers from a complex mixture of molecules. An analogous use of NMR to classify tumours is disclosed in Hagberg, NMR Biomed. 11: 148-56 (1998), for example. Additional procedures include nucleic acid amplification technologies, which may be used to generate a profile of biomarkers without physical separation of individual biomarkers. (See Stordeur et al., J. Immunol. Methods 259: 55-64 (2002) and Tan et al., Proc. Nat. Acad. Sci. USA 99: 11387-11392 (2002), for example). In one embodiment, laser desorption/ionization time-of-flight mass spectrometry is used to create a profile of biomarkers where the biomarkers are proteins or protein fragments that have been ionized and vaporized off an immobilizing support by incident laser radiation. A profile is then created by the characteristic time-of-flight for each protein, which depends on its mass-to-charge ("m/z") ratio. A variety of laser desorption/ionization techniques are known in the art. (See, e.g., Guttman et al., Anal. Chem. 73: 1252-62 (2001) and Wei et al., Nature 399:243-46 (1999)). Laser desorption/ionization time-of-flight mass spectrometry allows the generation of large amounts of information in a relatively short period of time. A biological sample is applied to one of several varieties of a support that binds all of the biomarkers, or a subset thereof, in the sample. Cell lysates or samples are directly applied to these surfaces in volumes as small as 0.5 μl, with or without prior purification or fractionation. The lysates or sample can be concentrated or diluted prior to application onto the support surface. Laser desorption/ionization is then used to generate mass spectra of the sample, or samples, in as little as three hours.

In a preferred embodiment, the protein biomarker profile is established using immunoassay technologies such as direct ELISA, indirect ELISA, sandwich ELISA, competitive ELISA, multiplex ELISA, radioimmunoassay, ELISPOT technologies, and other similar techniques known in the art.

The direct ELISA uses the method of directly labelling the antibody itself. Microwell plates are coated with a sample containing the target antigen, and the binding of labelled antibody is quantitated by a colorimetric, chemiluminescent, or fluorescent end-point. Since the secondary antibody step is omitted, the direct ELISA is relatively quick, and avoids potential problems of cross-reactivity of the secondary antibody with components in the antigen sample. However, the direct ELISA requires the labelling of every antibody to be used, which can be a time-consuming and expensive proposition. In addition, certain antibodies may be unsuitable for direct labelling. Direct methods also lack the additional signal amplification that can be achieved with the use of a secondary antibody.

The indirect, two-step ELISA method uses a labelled secondary antibody for detection. First, a primary antibody is incubated with the antigen. This is followed by incubation with a labelled secondary antibody that recognizes the primary antibody. For ELISA it is important that the antibody enzyme conjugate is of high specific activity. This is achieved when the antibody is affinity purified and the enzyme conjugation chemistry preserves antibody specificity as well as enzyme activity.

The sandwich ELISA measures the amount of antigen between two layers of antibodies. The antigens to be measured must contain at least two antigenic sites, capable of binding to the antibody, since at least two antibodies act in the sandwich. For this reason, sandwich assays are restricted to the quantitation of multivalent antigens such as proteins or polysaccharides. Sandwich ELISAs for quantitation of antigens are especially valuable when the concentration of antigens is low and/or they are contained in high concentrations of contaminating protein. To utilize this assay, one antibody (the "capture" antibody) is purified and bound to a solid phase typically attached to the bottom of a plate well. Antigen is then added and allowed to complex with the bound antibody. Unbound products are then removed with a wash, and a labelled second antibody (the "detection" antibody) is allowed to bind to the antigen, thus completing the "sandwich". The assay is then quantitated by measuring the amount of labelled second antibody bound to the matrix, through the use of a colorimetric substrate. Major advantages of this technique are that the antigen does not need to be purified prior to use, and that these assays are very specific. However, one disadvantage is that not all antibodies can be used. Monoclonal antibody combinations must be qualified as "matched pairs", meaning that they can recognize separate epitopes on the antigen so they do not hinder each other's binding. The ELISA kits are good enough to reach detection sensitivity at sub-nanogram per ml level and are useful for screening protein targets and quantifying their expression in different conditions. For higher detection sensitivity needed, monoclonal antibodies can be further introduced into the ELISA kit to pair with polyclonal IgY as either capture or detection antibodies.

When two "matched pair" antibodies are not available for a target, another option is the competitive ELISA. The advantage to the competitive ELISA is that non-purified primary antibodies may be used. Although there are several different configurations for competitive ELISA, one reagent must be conjugated to a detection enzyme, such as horseradish peroxidase. The enzyme may be linked to either the antigen or the primary antibody. One example of a competitor is a labelled antigen. In this type of ELISA, there is an inverse relationship between the signal obtained and the concentration of the analyte in the sample, due to the competition between the free analyte and the ligand-enzyme conjugate for the antibody coating the microplate, i.e. the more analyte the lower the signal. Briefly, an unlabeled purified primary antibody is coated onto the wells of a 96 well microtiter plate. This primary antibody is then incubated with unlabeled standards and unknowns. After this reaction is allowed to go to equilibrium, conjugated antigen is added. This conjugate will bind to the primary antibody wherever its binding sites are not already occupied by unlabeled antigen. Thus, the more unlabeled antigens in the sample or standard, the lower the amount of conjugated antigen bound. The plate is then developed with substrate and colour change is measured.

Multiplex ELISA is a microtiter plate ELISA-based protein array assay that allows simultaneous detection of multiple analytes at multiple array addresses within a single well. Different types of multiplex ELISA have been developed and are in practice. One of the examples is to measure antigens by coating or printing capture antibodies in an array format within a single well to allow for the construction of "sandwich" ELISA quantification assays. Generally, multiplex ELISA can also be achieved through antibody array, where different primary antibodies can be attached to a solid phase e.g. a glass plate to capture corresponding antigens in a biological sample. The detection method can be direct or indirect, sandwich or competitive, labelling or non-labelling, depending upon antibody array technologies.

The Enzyme-Linked Immunosorbent Spot (ELISpot) assay employs the sandwich assay approach of the Enzyme-Linked ImmunoSorbent Assay (ELISA), with some variations. The capture antibody is coated aseptically onto a polyvinylidene difluoride (PVDF)-backed microwell plate. The plate is blocked with serum proteins, cells of interest are plated out at varying densities, along with antigen or mitogen, and plates are incubated at 37° C. Cytokine secreted by activated cells is captured locally by the coated antibody on the high surface area PVDF membrane. The wells are washed to remove cells, debris, and media components. A second antibody (biotinylated) reactive with a distinct epitope of the target cytokine is employed to detect the captured cytokine. The detected cytokine is then visualized using avidin-HRP, and a precipitating substrate (e.g. AEC). The coloured end product (spot) represents an individual cytokine-producing cell. The spots can be counted manually (e.g., with a dissecting microscope) or using an automated reader to capture the microwell images and to analyze spot number and size.

Radioimmunoassay (RIA) involves mixing known quantities of radioactive antigen (frequently labelled with gamma-radioactive isotopes of iodine attached to tyrosine) with antibody to that antigen, then adding unlabeled or "cold" antigen and measuring the amount of labelled antigen displaced. Initially, the radioactive antigen is bound to the antibodies. When "cold" (unlabeled, quest) antigen is added, the two compete for antibody binding sites—at higher concentrations of "cold" antigen, more of it binds to the antibody, displacing the radioactive variant. The bound antigens are separated from the unbound ones.

As used herein, the term "profile" includes any set of data that represents the distinctive features or characteristics associated with a condition of sepsis. The term encompasses a "nucleic acid profile" that analyzes one or more genetic markers, a "protein profile" that analyzes one or more biochemical or serological markers, and combinations thereof. Examples of nucleic acid profiles include, but are not limited to, a genotypic profile, gene copy number profile, gene expression profile, DNA methylation profile, and combinations thereof. Non-limiting examples of protein profiles include a protein expression profile, protein activation profile, protein cleavage profile, and combinations thereof. For example, a "genotypic profile" includes a set of genotypic data that represents the genotype of one or more genes associated with a condition of sepsis. Similarly, a "gene copy number profile" includes a set of gene copy number data that represents the amplification of one or more genes associated with a condition of sepsis. Likewise, a "gene expression profile" includes a set of gene expression data that represents the mRNA levels of one or more genes associated with a condition of sepsis. In addition, a "DNA methylation profile" includes a set of methylation data that represents the DNA methylation levels (e.g., methylation status) of one or more genes associated with a condition of sepsis. Furthermore, a "protein expression profile" includes a set of protein expression data that represents the levels of one or more proteins associated with a condition of sepsis. Moreover, a "protein activation profile" includes a set of data that represents the activation (e.g., phosphorylation status) of one or more proteins associated with a condition of sepsis. A "protein cleavage profile" includes a set of data that represent the proteolytic cleavage of one or more proteins associated with a condition of sepsis.

The term "subject" or "patient" typically includes humans, but can also include other animals such as, e.g., other primates, rodents, canines, felines, equines, ovines, porcines, and the like.

The term "sample" as used herein includes any biological specimen obtained from a subject. Samples include, without limitation, whole blood, plasma, serum, red blood cells, white blood cells (e.g., peripheral blood mononuclear cells), saliva, urine, stool (i.e., faeces), tears, sweat, sebum, nipple aspirate, ductal lavage, tumour exudates, synovial fluid, cerebrospinal fluid, lymph, fine needle aspirate, amniotic fluid, any other bodily fluid, cell lysates, cellular secretion products, inflammation fluid, semen and vaginal secretions. In preferred embodiments, the sample is whole blood or a fractional component thereof such as plasma, serum, or a cell pellet. Preferably the sample is readily obtainable by minimally invasive methods. Samples may also include tissue samples and biopsies, tissue homogenates and the like.

In this respect, the invention provides for a method of establishing a healthy reference biomarker profile comprising the steps of:
(a) determining a quantity of at least two biomarkers selected from the group consisting of TREM-like-transcript-1 (TLT-1/TREML1), NGAL, TREM-1, Procalcitonin (PCT) and c-Reactive Protein (CRP) in a sample obtained from a subject not having a condition related to sepsis or SIRS; and
(b) storing the quantity of the selected biomarkers in the healthy subject sample in the form of a reference biomarker profile.

In addition, the invention provides for a method for establishing a SIRS reference biomarker profile comprising the steps of:
(a) determining a quantity of at least two biomarkers selected from the group consisting of TREM-like-transcript-1 (TLT-1/TREML1), NGAL, TREM-1, Procalcitonin (PCT) and c-Reactive Protein (CRP) in a sample obtained from a subject having a condition of SIRS; and
(b) storing the quantity of the selected biomarkers in the SIRS sample in the form of a reference biomarker profile.

Alternatively, the invention provides for a method for establishing a sepsis reference biomarker profile comprising the steps of:
(a) determining a quantity of at least two biomarkers selected from the group consisting of TREM-like-transcript-1 (TLT-1/TREML1), NGAL, TREM-1, Procalcitonin (PCT) and c-Reactive Protein (CRP) in a sample obtained from a subject having a condition related to sepsis; and
(b) storing the quantity of the selected biomarkers in the sepsis sample in the form of a reference biomarker profile.

In any one of the methods defined herein, the use of the TLT-1 marker is preferred, alone or in combination with any one of the markers selected from the group consisting of: NGAL, TREM-1, Procalcitonin (PCT) and C-reactive protein (CRP).

In any one of the methods defined herein, the combination of TLT-1 and NGAL, is preferred.

Especially in respect to the disclosures of Gibot et al., 2007 (Scand J Infect Dis. 39(6-7):604-8) and Tejera et al., 2007, (Cytokine 38(3):117-23), it is clear that the combined use of the TREM-1 biomarker in either BAL or serum can be indicative of sepsis.

In combination with the present invention, it would thus be highly preferred to combine the use of the TREM-1 and TLT-1 biomarker for prognosing sepsis. This is even more the case because of the opposite behaviour of the expression levels of the TLT-1 and TREM-1 biomarker in healthy versus sepsis subjects. As reported previously in the literature, the TREM-1 marker is up-regulated in sepsis subjects vs. healthy subjects, while the present invention shows that the TLT-1 expression is down-regulated in sepsis vs. healthy subjects. Both biomarkers are detectable in serum and form due to their opposite behaviour an improved prognostic tool for sepsis when used in combination.

In any one of the methods defined herein, the combination of TLT-1 and TREM-1 is particularly preferred.

In any one of the methods defined herein, the combination of TLT-1 and TREM-1 in combination with any one of the remaining markers selected from the group consisting of: NGAL, Procalcitonin (PCT) and C-reactive protein (CRP) is also preferred.

In any one of the methods defined herein, the combination of TLT-1, TREM-1 and Procalcitonin (PCT) is particularly preferred.

Kits

The invention also provides kits for predicting, prognosis and/or diagnosis of sepsis in a subject. The kits of the present invention comprise at least one biomarker of the present invention or molecules specifically binding thereto. Specific biomarkers that are useful in the present invention are those selected from the group consisting of: TREM-like-transcript-1 (TLT-1/TREML1), NGAL, TREM-1, Procalcitonin (PCT) and C-reactive protein (CRP) but a kit may include one or two or three or four or all of the biomarkers listed therein with or without other biomarkers in addition.

The biomarker or biomarkers in each kit may be part of an array, or the biomarker(s) may be packaged separately and/or individually. The kit may also comprise at least one standard to be used in generating the biomarker profiles of the present invention. The kits of the present invention also may contain reagents that can be used to detectably label biomarkers contained in the biological samples from which the biomarker profiles are generated. For this purpose, the kit may comprise a set of antibodies or functional fragments thereof that specifically bind to one or more of the biomarkers selected from the group consisting of: TREM-like-transcript-1 (TLT-1/TREML1), NGAL, TREM-1, Procalcitonin (PCT) and C-reactive protein (CRP) and/or any other biomarkers that are included in creating the profile.

The invention also provides a method and a kit for assessing the occurrence and stage or severity of sepsis in a subject, which can range from the very onset of sepsis, to septic shock and eventually the death of the subject, by measuring the quantity of one or of a combination of one or more of the biomarkers of the present invention selected from the group consisting of TREM-like-transcript-1 (TLT-1/TREML1), NGAL, TREM-1, Procalcitonin (PCT) and c-Reactive Protein (CRP) in combination with known biomarkers for sepsis or SIRS, in the sample from the subject and comparing the biomarker measurements to that of a sample obtained from a healthy or non-sepsis subject. The invention provides a means for a clinician to estimate the degree of sepsis at an initial assessment, and to monitor the change in status of the sepsis (worsening, improving, or remaining the same) based on the detected amount of the one or more biomarkers in the sample of the subject.

Typically, the clinician would establish a protocol of collecting and analyzing a quantity of fresh sample from the patient at selected intervals. Typically the sample is obtained intermittently during a prescribed period. The period of time between intermittent sampling may be dictated by the condition of the subject, and can range from a sample each 24 hours to a sample taken continuously, more typically from each 4 hours to each 30 minutes.

Using the methods and techniques described herein, both a qualitative level of one or more of the biomarkers present in the sample can be analyzed and estimated, and a quantitative level of one or more of the biomarkers present in the sample can be analyzed and measured. The clinician would select the qualitative method, the quantitative method, or both, depending upon the status of the patient. Typically, the quantity of sample to be collected is less than 10 milliliters, less than 1 milliliter, and more typically less than 10 µl. A typical sample can range from about 1 µl to about 1 ml. Typically the larger quantities of sample (about 10 ml) are used for quantitative assays. Typically, these small amounts of sample are easily and readily available or obtainable from clinical subjects who are either prone to developing sepsis, or have developed sepsis.

Once an indication of sepsis has been detected, and intervention and treatment of the disease or condition has commenced, the clinician can employ the method and kit of the invention to monitor the progress of the treatment or intervention. Typically, one or more subsequent post-treatment samples will be taken and analyzed for the presence of one or more of the biomarkers as the treatment of the sepsis condition commences and continues. The treatment is continued until the presence of one or more of the biomarkers of the present invention in subsequent post-treatment samples is normalized when compared to a sample obtained from a healthy or non-sepsis subject. As the treatment and intervention ameliorate the condition, the expression of one or more of the biomarkers, and its presence in the sample, will be altered and normalized when compared to a sample of a healthy or non-sepsis subject. The degree of amelioration will be expressed by a correspondingly normalized level of one or more of the biomarkers, detected in a sample. As the condition nears complete recovery, the method can be used to detect the complete normalization of one or more of the biomarkers of the invention, signalling the completion of the course of treatment.

The term "binding molecule" refers to all suitable binding molecules that are specifically binding or interacting with one of the biomarkers of the invention and that can be used in the methods and kits of the present invention. Examples of suitable binding agents are antibodies, aptamers, specifically interacting small molecules, specifically interacting proteins, and other molecules that specifically bind to one of the biomarkers. Both monoclonal and polyclonal antibodies that bind one of the biomarkers of the present invention are useful in the methods and kits of the present invention. The monoclonal and polyclonal antibodies can be prepared by methods known in the art and are often commercially available.

Aptamers that bind specifically to the biomarkers of the invention can be obtained using the so called SELEX or Systematic Evolution of Ligands by EXponential enrichment. In this system, multiple rounds of selection and amplification can be used to select for DNA or RNA molecules with high specificity for a target of choice, developed by Larry Gold and co-workers and described in U.S. Pat. No. 6,329,145. Recently a more refined method of designing so-called photoaptamers with even higher specificity has been described in U.S. Pat. No. 6,458,539 by the group of Larry Gold.

Methods of identifying binding agents such as interacting proteins and small molecules are also known in the art. Examples are two-hybrid analysis, immunoprecipitation methods and the like.

Typically, the step of detecting the complex of the capture antibody and one or more of the biomarkers comprises contacting the complex with a second antibody for detecting the biomarker.

The method for detecting the complex of one or more of the biomarkers and the primary antibody or binding molecule comprises the steps of: separating any unbound material of the sample from the capture antibody-biomarker complex; contacting the capture antibody-biomarker complex with a second antibody for detecting the biomarker, to allow formation of a complex between the biomarker and the second antibody; separating any unbound second antibody from the biomarker-second antibody complex; and detecting the second antibody of the biomarker-second antibody complex.

A kit for use in the method typically comprises one or more media having affixed thereto one or more capture antibodies or binding molecules, whereby the sample is contacted with the media to expose the capture antibody or binding molecule to the biomarker present in the sample. The kit includes an acquiring means that can comprise an implement, such as a spatula or a simple stick, having a surface comprising the media. The acquiring means can also comprise a container for accepting the sample, where the container has a sample-contacting surface that comprises the media. In another typical embodiment, the assay for detecting the complex of one or more of the biomarkers and the antibody or binding molecule can comprise an ELISA, and can be used to quantify the amount of one or more the biomarkers in a sample. In an alternative embodiment, the acquiring means can comprise an implement comprising a cassette containing the media.

Early detection of one or more of the biomarkers of the present invention can provide an indication of the presence of the protein in a sample in a short period of time. Generally, a method and a kit of the present invention can detect the biomarker in a sample within four hours, more typically within two hours, and most typically within one hour, following the sepsis condition. Preferably, the biomarker can be detected within about 30 minutes following the sepsis condition.

A rapid one-step method of detecting one or more of the biomarkers of the present invention can reduce the time for detecting the sepsis condition. A typical method can comprise the steps of: obtaining a sample suspected of containing one or more of the biomarkers; mixing a portion of the sample with one or more detecting antibodies or binding molecules that each specifically bind to one of the biomarkers, so as to initiate the binding of the detecting antibody or binding molecule to the biomarkers in the sample; contacting the mixture of sample and detecting antibody or binding molecule with an immobilized capture antibody or binding molecule which specifically binds to the biomarker, which capture antibody or binding molecule does not cross-react with the detecting antibody or binding molecule, so as to bind the detecting antibody or binding molecule to the biomarker, and the biomarker to the capture antibody or binding molecule, to form a detectable complex; removing unbound detecting antibody or binding molecule and any unbound sample from the complex; and detecting the detecting antibody or binding molecule of the complex. The detectable antibody or binding molecule can be labelled with a detectable marker, such as a radioactive label, a fluorescent label, an enzyme label, a biological dye, a magnetic bead, (strept)avidin, or biotin, as is well known in the art.

In the kits according to the present invention, detection of the TLT-1 biomarker is preferably envisaged, alone or in combination with one or more of the biomarkers selected from the group consisting of: NGAL, TREM-1, Procalcitonin (PCT) and c-Reactive Protein (CRP), wherein the combination of TLT-1 and NGAL is preferred, the combination of TLT-1, TREM-1 and PCT is preferred and the combination of TLT-1 and TREM-1 is particularly preferred.

Use of the Present Invention in Treatment and Diagnosis, Prediction and/or Prognosis Diagnosis, Prediction, and/or Prognosis of Sepsis and Sepsis Versus SIRS In one aspect of the invention there is provided a method for the prediction, prognosis and/or diagnosis of SIRS, sepsis, severe sepsis and MODS or for the differentiation between said septic conditions in a subject comprising obtaining a candidate biomarker profile from a biological sample taken from said subject wherein said candidate biomarker profile is based on the measurement of the quantity of one or more of the biomarkers selected from the group consisting of TREM-like-transcript-1 (TLT-1/TREML1), NGAL, TREM-1, Procalcitonin (PCT) and c-Reactive Protein (CRP) pro-Hepcidin (pro-HEPC) in said sample, and comparing said candidate biomarker profile with a reference biomarker profile obtained form a healthy subject.

Also provided by the invention is a method for the prediction, prognosis and/or diagnosis of sepsis or for the differentiation between SIRS and sepsis in a subject comprising: obtaining a candidate biomarker profile from a biological sample taken from said subject wherein said candidate biomarker profile is based on at least one or two biomarkers selected from the group consisting of TREM-like-transcript-1 (TLT-1/TREML1), NGAL, TREM-1, Procalcitonin (PCT) and c-Reactive Protein (CRP) and comparing said candidate profile with a reference biomarker profile obtained form a healthy subject or a patient having SIRS.

The invention further provides for a method for prediction, prognosis and/or diagnosis of sepsis or for the differentiation between SIRS and sepsis in a subject comprising measuring the level of at least one or two biomarkers selected from the group consisting of TREM-like-transcript-1 (TLT-1/TREML1), NGAL, TREM-1, Procalcitonin (PCT) and c-Reactive Protein (CRP) in a biological sample from said subject; using said measurements obtained in step a) to create a profile for said biomarkers; and comparing said profile with a reference biomarker profile obtained form a healthy subject or a patient having SIRS.

In a further embodiment, the invention provides for prediction, prognosis and/or diagnosis of sepsis or for the differentiation between SIRS and sepsis in a subject comprising determining a quantity of at least one or two biomarkers selected from the group consisting of TREM-like-transcript-1 (TLT-1/TREML1), NGAL, TREM-1, Procalcitonin (PCT) and c-Reactive Protein (CRP) in a sample obtained from a subject; and comparing the quantity of the selected biomarkers in the test subject sample with a range of normal values of the selected biomarkers in control subjects; whereby an increase or decrease in the quantity of the selected biomarker in the sample to a level higher or lower than the range of normal values of the selected biomarkers is indicative of sepsis.

In a further aspect the invention provides for a method for prediction, prognosis and/or diagnosis of sepsis or for the differentiation between SIRS and sepsis in a subject comprising determining a quantity of at least one or two biomarkers selected from the group consisting of TREM-like-transcript-1 (TLT-1/TREML1), NGAL, TREM-1, Procalcitonin (PCT) and c-Reactive Protein (CRP) and comparing the quantity of the selected biomarkers in the test subject sample with a range of values of the selected biomarkers obtained from subjects with sepsis; whereby a comparable quantity of the selected biomarkers in said sample to the range of values of the selected biomarkers in subjects with sepsis is indicative of sepsis.

Alternatively, the invention provides for a method for the prediction, prognosis and/or diagnosis of sepsis or the differentiation between SIRS and sepsis in a subject comprising obtaining a candidate antibody profile from a biological sample taken from said individual wherein said candidate antibody profile is based on an antibody to at least one or two biomarkers selected from the group consisting of TREM-like-transcript-1 (TLT-1/TREML1), NGAL, TREM-1, Procalcitonin (PCT) and c-Reactive Protein (CRP) and comparing said candidate antibody profile with a reference antibody profile.

In a further embodiment, the invention provides for a method for determining whether an individual is responsive to treatment for sepsis with a substance, comprising the steps of obtaining a candidate biomarker profile from a biological sample taken from said individual wherein said candidate biomarker profile is based on at least one or two biomarkers selected from the group consisting of TREM-like-transcript-1 (TLT-1/TREML1), NGAL, TREM-1, Procalcitonin (PCT) and c-Reactive Protein (CRP) and comparing said candidate profile with a reference biomarker profile.

As is shown in the examples below, the expression of the TLT-1 biomarker is reduced in patients with sepsis as compared to healthy subjects. Therefore, in a preferred embodiment, one of the selected biomarkers is TREML-1 (TLT-1).

In yet a further embodiment, the selected biomarkers are TREML-1 and TREM-1.

It is known from the prior art that the expression of TREM-1 is increased in sepsis patients as compared to healthy subjects. In combination with the results of the present invention that TLT-1 expression is decreased in sepsis patients, the combination of the TLT-1 marker and the TREM-1 marker is particularly preferred.

In another preferred embodiment, the combination of biomarkers is TREML-1 and TREM-1 in combination with any one of C-reactive protein (CRP), Procalcitonin (PCT) or NGAL.

Preferred samples to be analysed in the method of the present invention are blood or urine, more preferable the sample is serum or plasma.

In a preferred embodiment, the method of the invention uses immunoassay technology selected from the group of direct ELISA, indirect ELISA, sandwich ELISA, competitive ELISA, multiplex ELISA, radioimmunoassay, or ELISPOT technologies to establish the biomarker profile. In alternative embodiment, the biomarker profile is established using mass spectrometry analysis methods of the proteins present in said sample.

In a preferred embodiment, the methods indicated in the present invention are particularly useful to distinguish between SIRS and sepsis.

Treatment

Once a condition of sepsis has been diagnosed, the identification of the biomarkers of the present invention could be of use in the treatment or amelioration of the sepsis condition of the subject.

It is possible to increase the expression level or abundance of a protein in a subject by administrating such a purified, synthetically or recombinantly produced biomarker of the invention to a subject having a reduced level of said biomarker in comparison to a healthy subject. Administering agents that increase the expression or activity of said biomarker may also be beneficial to the patient. The presence of the sTNFR2 biomarker in blood obtained from a subject having sepsis for example is drastically reduced when compared to the samples of a subject having SIRS or a healthy subject.

Another possibility can be the reduction of the level or abundance of a certain biomarker of the invention in case said biomarker has an increased occurrence in the blood of patients having sepsis when compared to the samples of a subject having SIRS or a healthy subject. Examples of these biomarkers are TREM-like-transcript-1 (TLT-1/TREML1), NGAL, TREM-1, Procalcitonin (PCT) and C-reactive protein (CRP) Administering agents that reduce the expression or activity of said proteins may be beneficial to the subject.

EXAMPLES

The following experimental details describe the complete exposition of one embodiment of the invention as described above and are not to be deemed limiting of the invention in any way.

Example 1

Identification of New Biomarkers for Sepsis in a Mouse Sepsis Model

We used a mouse sepsis model in order to identify new sepsis biomarkers. At day 0, the mice were injected with PBS (control) or Salmonella (infected). Blood samples were taken from both control and infected mice every 24 h by retro-orbital bleeding. Mice of the infected group show no immediate signs of disease just after infection, but suddenly become ill after 4-5 days and then die within 24 h. In the obtained blood samples, we analysed the changes in protein expression using mass spectrometric detection of protein levels using our previously published COFRADIC™ technology platform.

All serum samples were depleted for the most abundant proteins using an Agilent column. Depletion efficiency was checked using ELISA and Western Blot analysis. The reference pool was prepared at this stage and this reference was considered as a normal sample for the rest of process. Samples were prepared for MASStermind™ analysis according the standard N-terminal COFRADIC™ procedures. Reference pool and samples were differentially labelled by trypsin mediated incorporation of $^{18}O/^{16}O$, where the different samples carried the heavy oxygen label and the reference the $^{16}O$. Just before COFRADIC™ sorting each sample was mixed with the reference at equal protein masses. After sorting and NanoLC separations, MS spectra were obtained. MS data were de-isotoped, clustered and features were constructed using in house developed software called euCatLabel. The output of this data processing is an expression matrix containing all features from all analyzed samples. Each feature is represented by a unique combination of m/z, COFRADIC™ sorting pool and NanoLC retention time and features can be present in a number of samples ranging from 1 to all. If a feature is present in a sample it will carry a ratio, which represents intensity of the feature in the reference sample (i.e. the $^{16}O$ peak) over the intensity in the respective sample (the $^{18}O$ peak). Recurrent quantifiable features are features with a reliable ratio reading in at least two samples.

In the time course analysis protein profiles were compared of PBS controls at day 4, mice just before infection with Salmonella, at day 1 after infection and at day 4 and day 5 after infection (see FIG. 1). In order to obtain biomarkers for long-term response, we analysed proteins differing at least 2-fold between d1 and d4 after infection, but who did not change significantly between d0 and PBS controls or showed a change just after infection (d0 vs. d1). For biomarkers useful in short term diagnosis, i.e. diagnosis of infection, we looked at proteins having a two fold increase in expression between control mice and d1 infected mice and did not change in response to sterss from daily bleeding (control vs. d0). This analysis yielded us 80 protein groups that showed a trend during the course of infection and sepsis development. From these 2 biologically relevant biomarkers were eventually retained: Neutrophil gelatinase-associated lipocalin (NGAL) and TREM-like-transcript-1 (TRML1/TLT1).

Example 2

Verification of the COFRADIC™ Results in Blood Samples Obtained Through the Mouse Sepsis Model In order to verify the results of the N-terminal COFRADIC™ technology as outlined above, we performed ELISA and Western blot experiments on both markers in the blood samples obtained from the mice in the test set-up (i.e. PBS-injected control mice and mice infected with Salmonella at d0, blood samples taken at d0-d7.) As can be seen from the figures, the NGAL expression in the mice blood samples increases between d1 and d4 after infection (25-fold increase) and keeps increasing up to d5, in an analogous manner to the COFRADIC™ measurements, thereby confirming the COFRADIC™ identification of a change in protein level during sepsis in the mouse model. These results were further confirmed in an independent set of mouse samples.

Also for the TREM-like-transcript-1 biomarker, we could compare the test results obtained from the COFRADIC™ technology platform with Western-blot analysis of blood samples obtained from control mice and from mice infected with salmonella from d0 to d7. Again, comparable results were obtained with both the COFRADIC™ technology platform and the standard Western blot protein level analysis, i.e. a down regulation of TREM-like1, again confirming the accuracy of the COFRADIC™ technology. Note that only the soluble TREM-like-transcript-1 is detected in serum from mice (20 kDa). This makes sense since TREM-like transcript-1 is a platelet membrane bound receptor (full-length=30 kDa), which is secreted, thereby ending up in the serum, if the membrane anchor is cleaved from the rest of the protein, resulting in the soluble protein part.

Example 3

Confirmation of the Biomarkers in Human Sepsis Samples

In order to be able to extrapolate the test results in the mouse sepsis model to human sepsis prognosis and diagnosis, we analysed the expression level of NGAL in human samples obtained from patients having either SIRS or Septic MODS. ELISA results of NGAL expression in human sepsis samples as compared to healthy samples confirmed again that, although the error margin is quite large due to the small sample size, the human NGAL protein is also up-regulated in human SIRS and sepsis (MODS) samples as compared to samples obtained from healthy subjects.

For TREM-like-transcript-1 the same was done, with comparable results, confirming TREM-like-transcript-1 as being a new candidate sepsis marker.

In order to increase the sensitivity, an immuno-precipitation step was included prior to Western Blot. This immuno-precipitation was performed on human serum & plasma from healthy controls and also on serum from patients suffering from sepsis and severe sepsis. For this immuno-precipitation a monoclonal rat anti-human-TREM-like-transcript-1 antibody was used to capture the TREM-like-transcript-1 proteins on protein A beads. After an overnight binding step, elution of the TREM-like-transcript-1 proteins was done in non-reducing conditions. Following this IP, a Western Blot analysis was performed using a polyclonal goat anti-human-TREM-like-transcript-1, followed by an anti-goat IgG HRP-coupled antibody for chemiluminescent detection. Since TREM-like-transcript-1 is a membrane-bound protein which is abundant in the α-granules of resting platelets and on the surface of activated platelets (Gattis et al., 2006; J Biol Chem. 281, 13396-403, 2006), platelet lysate served as a positive control in this experiment.

The performed experiments resulted in the following conclusions:

1. TREM-like-transcript-1 is detectable in human serum, but not in human plasma. A double band at masses 14 kDa and 12 kDa is visible in serum (FIG. 1, panel A), corresponding to the data presented in literature by Gattis (Gattis et al., 2006). The positive control shows 2 bands. One band lies at 35 kDa and represents the full length form of TREM-like-transcript-1, the other band is situated at approximately 22 kDa and represents the soluble form of TREM-like-transcript-1. The reason for the lower mass of the doublet in serum in comparison with this 20 kDa band in platelet lysate still needs to be elucidated.
2. The down regulation of TREM-like-transcript-1 serum levels, as shown by the COFRADIC™ technology, were confirmed since the doublet is clearly visible in serum from the healthy individuals, only slightly visible in the serum from patients suffering from sepsis and not visible in the serum from the patient suffering from severe sepsis (equal loading was applied and checked after development of the Blot) (FIG. 1, panel B).

Because of the specific expression of TREM-like-transcript-1 on platelets, the down regulation of this protein might correlate with the platelet count rather than disease severity. However, platelet counts were compared with the other data and no correlation was found, leading to the conclusion that serum levels of TREM-like-transcript-1 are indicative of disease severity in sepsis.

Example 4

Figure 9:
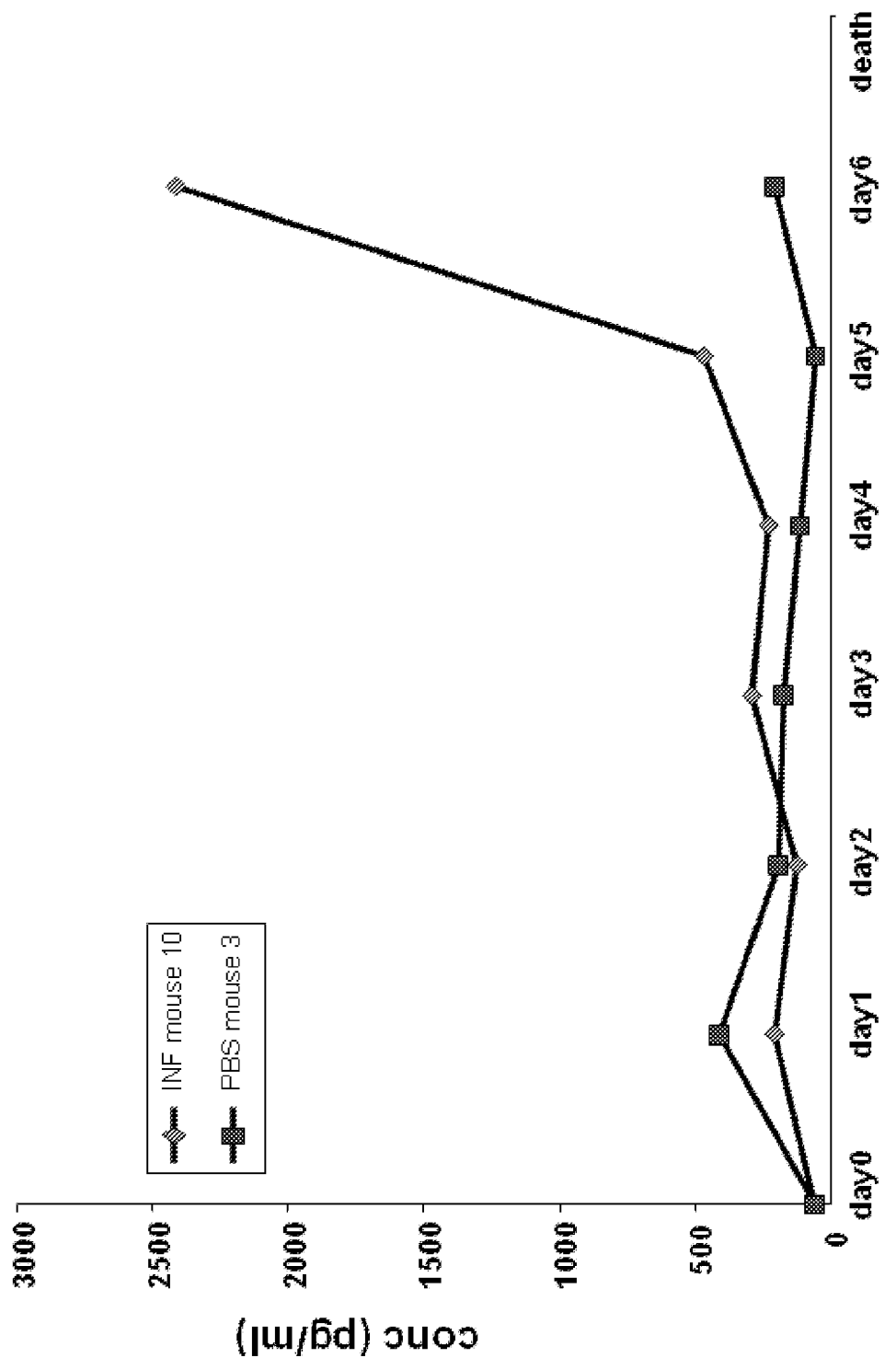
FIG. 9: ELISA measurements of TREM-1 on a set of infected and control mouse samples illustrating up regulation of TREM-1 during course of infection and sepsis development, i.e. inverse correlation to TREML-1.
Figure 10:
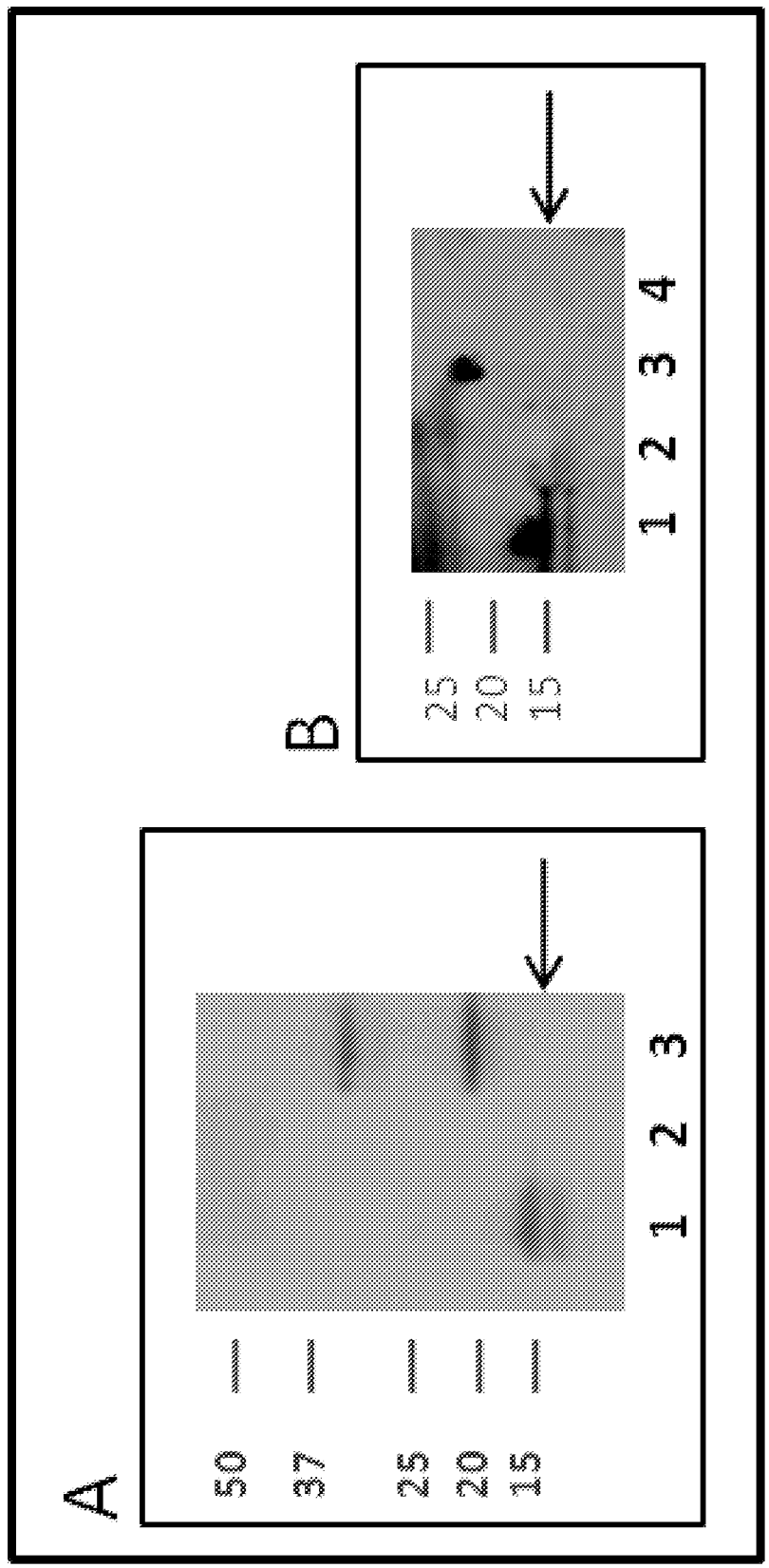
FIG. 10: Panel A: Western Blot analysis of human serum and human platelets. Lane 1, immunoprecipitation (IP) on serum from healthy individual, using mAb against TLT-1. Lane 2, IP on 1 ml serum from healthy individual, without mAb against TLT-1 (Negative Control). Lane 3, IP on human platelet lysate, using mAb against TLT-1. Panel B: Western Blot analysis of human serum from healthy vs. patients suffering from sepsis and severe sepsis. Lane 1, IP on serum from a healthy individual. Lane 2 3, IP on serum from septic patients, Lane 4, IP on serum from patient with severe sepsis.

Inverse Correlation Between TREM-Like-Transcript-1 and TREM-1 Expression in Sepsis Models It is known that TREM-1 is a sepsis marker, and is up-regulated in samples of sepsis patients versus healthy subjects. We have shown that the level of sTREML-1 expression is down-regulated when sepsis starts. Using the same model system we also examined the expression of TREM-1 in samples from infected and control groups at different time points after the challenge. From these we can see that while sTREML-1 is down regulated during the course of sepsis development, its family member TREM-1 shows the inverse change i.e. a clear up regulation at later time points after infection (see FIG. 9). These results confirm that the use of both biomarkers can lead to a very precise diagnostic and prognostic tool for SIRS, sepsis, severe sepsis and MODS.

Example 5

Combined Use of TREM-Like-Transcript-1 and TREM-1 to Improve Sepsis Diagnosis, Prognosis and/or Prediction In order to evaluate the usefulness of the combination of TREM-1 and TREM-like-transcript-1 in a single diagnostic test, we will analyze both markers in serum of a set of human SIRS, sepsis, severe sepsis and MODS samples and/or in other relevant sepsis models. For this either antibody based assays or mass-spectrometry based detection methods can be used.

In view of the results provide by the present invention regarding the TLT-1 marker, combined with the knowledge regarding the TREM-1 marker from the literature, it is anticipated that the combined detection of the TLT-1 and TREM-1 biomarkers in serum samples will enable a more precise prognosis of sepsis status in a subject, especially due to their opposite behaviour (TLT-1 down-regulation vs. TREM-1 up regulation).

Calculating the ratio of the serum expression levels of TREM-1 and TLT-1 would thereby create a statistically powerful tool for the efficient and accurate prognosis of sepsis, because the differences in expression level between healthy and diseased subjects would be emphasised.

Several publications and patent documents are referenced in this application in order to more fully describe the state of the art to which this invention pertains. The disclosure of each of these publications and documents is incorporated by reference herein.

While certain of the preferred embodiments of the present invention have been described and specifically exemplified above, it is not intended that the invention be limited to such embodiments. Various modifications may be made thereto without departing from the scope and spirit of the present invention, as set forth in the following claims.

What is claimed is:

1. A method for treating systemic inflammatory response syndrome (SIRS), sepsis, severe sepsis, septic shock, or multiple organ dysfunction score (MODS) in a subject having symptoms of, being diagnosed with, or being at risk of developing SIRS, sepsis, severe sepsis, septic shock, or MODS, wherein the method comprises:
   (a) identifying the subject as in need of treatment for SIRS, sepsis, severe sepsis, septic shock, or MODS by a method comprising:
      (i) providing a sample from the subject;
      (ii) measuring the level of at least biomarkers Triggering Receptor Expressed on Myeloid cells-1 (TREM-1) and TREM-like receptor transcript-1 (TLT1), in a biological sample from said subject;
      (iii) using said measurements obtained in step ii) to create a profile for said biomarkers; and
      (ii) comparing said profile with a reference biomarker profile obtained from a healthy subject, and finding a deviation of the profile of the sample from the subject with the reference biomarker profile, wherein an up-regulation of TREM-1 in combination with a down-regulation of TLT1, identifies the subject as in need of treatment for SIRS, sepsis, severe sepsis, septic shock, or MODS; and (b) treating the subject having the deviation with an antibiotic treatment or a fluid resuscitation treatment.

2. A method for prediction, prognosis and/or diagnosis of SIRS, sepsis, severe sepsis, septic shock, or MODS in a subject comprising:
   (a) creating an expression matrix by constructing features on a computer from samples obtained from a reference pool of healthy subjects or a reference pool of subjects having a condition related to SIRS, sepsis, severe sepsis, septic shock, or MODS, wherein the expression matrix comprises at least biomarkers human TREM-like receptor transcript-1 (TLT1) and TREM-1;
   (b) the quantity of the selected biomarkers in the reference pool in the form of a reference biomarker profile respectively for healthy subjects or subjects having a condition related to SIRS, sepsis, severe sepsis, septic shock, or MODS;
   (c) determining a quantity of the biomarkers human TREM-like receptor transcript-1 (TLT1) and TREM-1, in a sample obtained from a subject;
   (d) comparing the quantity of the selected biomarkers in the test subject sample with the reference biomarker profile; and
   (e) determining an increase or decrease in the quantity of the selected biomarkers in the sample compared to the reference biomarker profile, wherein an up-regulation of TREM-1 in combination with a down-regulation of TLT1 as compared to the reference biomarker profile is indicative of SIRS, sepsis, severe sepsis, septic shock, or MODS.

3. A method for treating systemic inflammatory response syndrome (SIRS), sepsis, severe sepsis, septic shock, or multiple organ dysfunction score (MODS) in a subject having symptoms of, being diagnosed with, or being at risk of developing SIRS, sepsis, severe sepsis, septic shock, or MODS, wherein the method comprises:
   (a) identifying the subject as in need of treatment for SIRS, sepsis, severe sepsis, septic shock, or MODS by a method comprising:
      (i) providing a sample from the subject;
      (ii) determining a quantity of at least biomarkers human TREM-like receptor transcript-1 (TLT1) and TREM-1; and
      (iii) comparing the quantity of the biomarkers in the test subject sample with a range of values of the selected biomarkers obtained from subjects with SIRS, sepsis, severe sepsis, septic shock, or MODS respectively; whereby a comparable quantity of the selected biomarkers in said sample to the range of values of the selected biomarkers in subjects with sepsis is indicative of SIRS, sepsis, severe sepsis, septic shock, or MODS respectively; and
   (b) treating the subject having the deviation with an antibiotic treatment, or a fluid resuscitation treatment.

4. The method of claim 1 further comprising determining whether the subject is responsive to treatment for SIRS, sepsis, severe sepsis, septic shock, or MODS with a substance, comprising the steps of:
   (a) obtaining a candidate biomarker profile from a biological sample taken from said subject wherein said candidate biomarker profile is based on at least biomarkers human TREM-like receptor transcript-1 (TLT1) and TREM-1; and
   (b) comparing said candidate profile with a reference biomarker profile from a healthy subject.

5. A method for establishing a reference biomarker profile comprising the steps of:
   (a) determining a quantity of at least biomarkers human TREM-like receptor transcript-1 (TLT1) and TREM 1 in samples obtained from a reference pool of healthy subjects or a reference pool of subjects having a condition related to SIRS, sepsis, severe sepsis, septic shock, or MODS;
   (b) processing data obtained from the samples by constructing features for the reference pool with a computer, and
   (c) storing the quantity of the selected biomarkers in the reference subject sample in the form of a reference biomarker profile respectively for healthy subjects or subjects having a condition related to SIRS, sepsis, severe sepsis, septic shock, or MODS.

6. A method for treating SIRS, sepsis, severe sepsis, septic shock, or MODS in a subject having symptoms of, being diagnosed with, or being at risk of developing SIRS, sepsis, severe sepsis, septic shock, or MODS, wherein the method comprises:
   (a) monitoring or determining prognosis of the sepsis-related condition in a subject comprising:
      (i) providing samples taken from the subject at two or more different time points;
      (ii) measuring the level of at least biomarkers TREM-like receptor transcript-1 (TLT1), and TREM-1 in said samples;
      (iii) comparing the quantity of the TREM-like receptor transcript-1 (TLT1), and TREM-1 between samples as measured in (ii) and finding a deviation or no deviation of the quantity of the TREM-like receptor transcript-1 (TLT1), and TREM-1 between the samples as measured in (ii);
      (iv) attributing said finding of deviation or no deviation in (iii) to a change in the sepsis-related condition of the subject between the two or more successive time points; and
   (b) treating the subject having the deviation with an antibiotic treatment or a fluid resuscitation treatment, wherein an up-regulation of TREM-1 in combination with a down-regulation of TLT1 in later samples as compared to earlier samples identifies the subject as having poor prognosis and in need of continued or altered treatment for SIRS, sepsis, severe sepsis, septic shock, or MODS.

* * * * *

UNITED STATES PATENT AND TRADEMARK OFFICE
CERTIFICATE OF CORRECTION

PATENT NO. : 8,697,370 B2  Page 1 of 1
APPLICATION NO. : 12/990841
DATED : April 15, 2014
INVENTOR(S) : Kas et al.

It is certified that error appears in the above-identified patent and that said Letters Patent is hereby corrected as shown below:

In the Drawings

Figure 5:
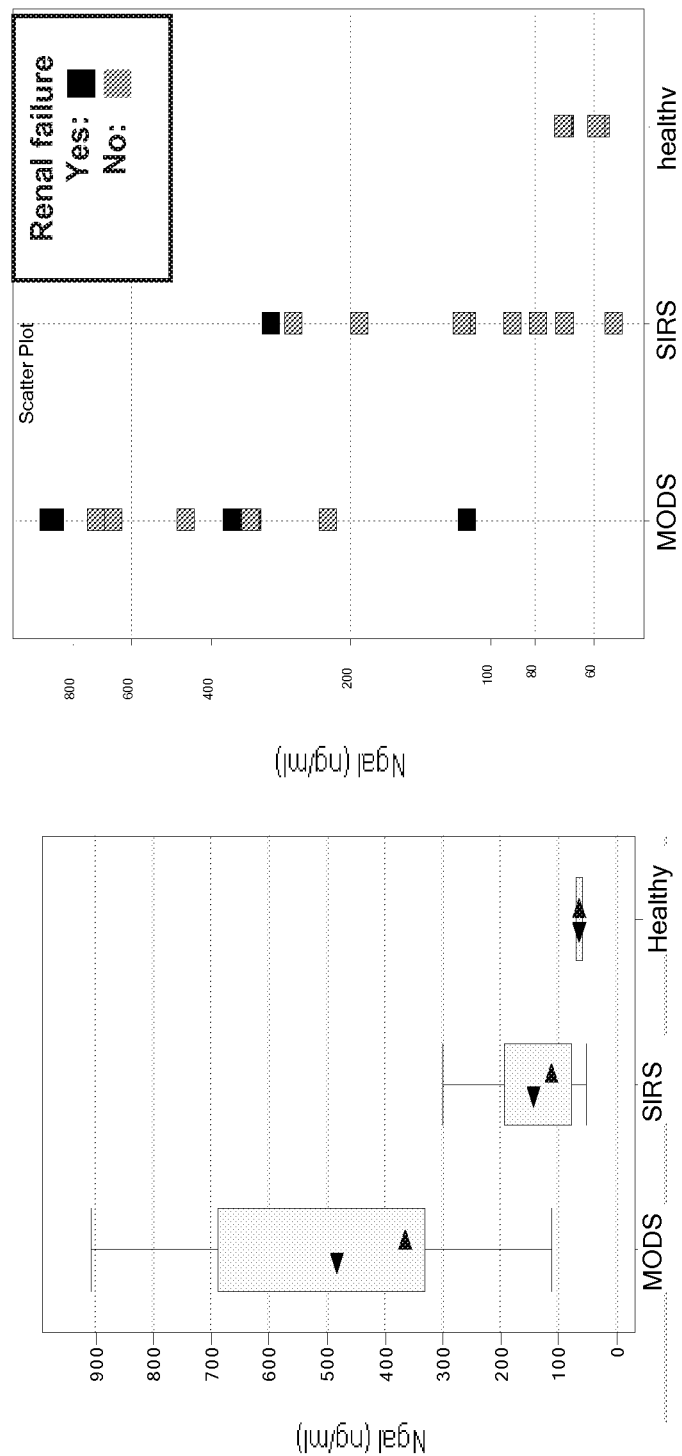
FIG. 5: Left hand graph: Analysis of NGAL expression by ELISA on human samples from sepsis-MODS patients (n=9), SIRS patients (n=11) and healthy subjects (n=4); Right hand graph: correlation to the occurrence of kidney failure, for which NGAL has been reported to be a marker.
Figure 6:
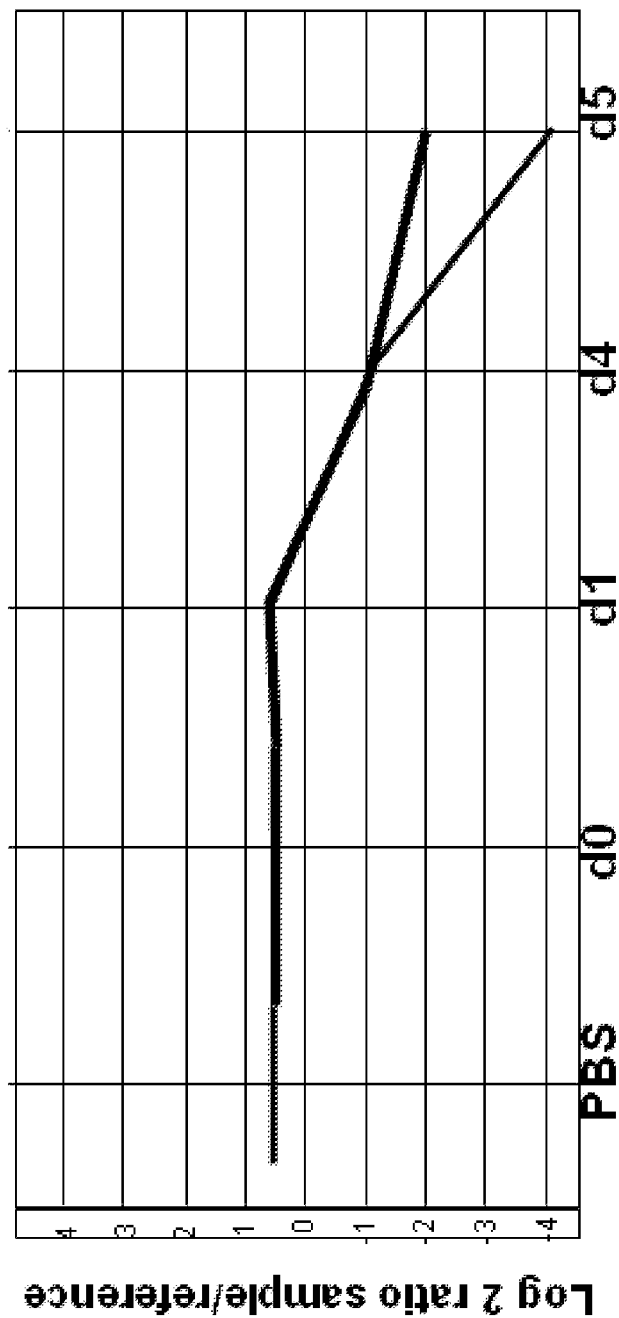
FIG. 6: Cofradic™ analysis of mouse sepsis samples and control samples envisaging the TREML-1 candidate biomarker. It becomes clear from this graph that the expression of TREML-1 is down-regulated during the course of sepsis in the mouse model system. Please note ratios shown are in log 2 scale. Two peptides are detected, probably the full-length and the soluble sTREML-1.
Figure 7:
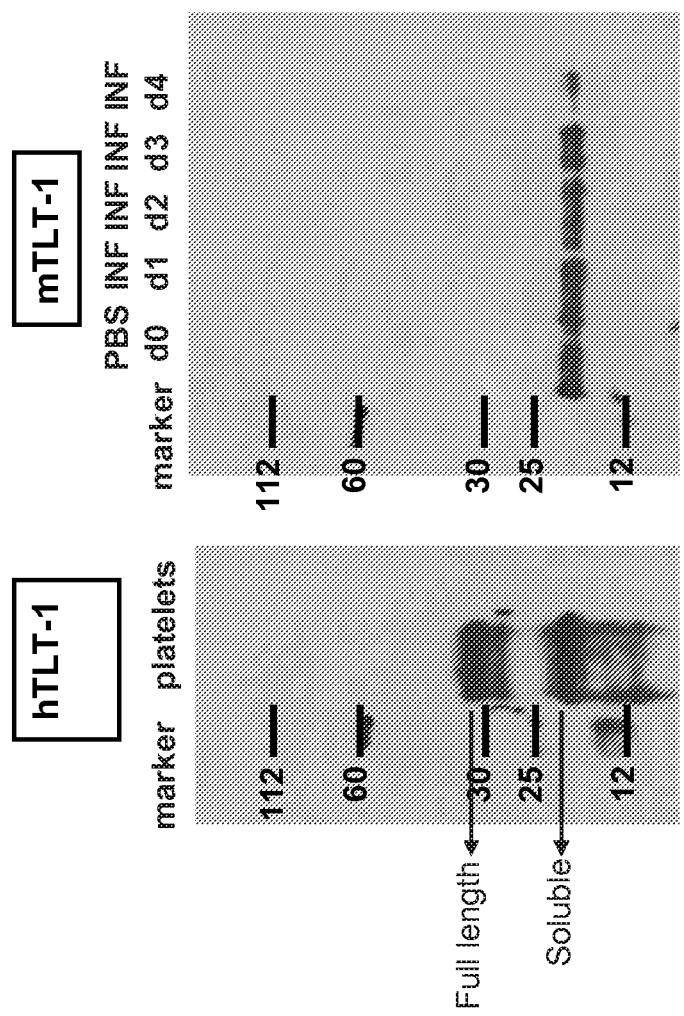
FIG. 7: Western blot analysis of the mouse depleted (IgG, Albumin, Transferrin) serum samples using an anti mouse TREML-1 antibody on the same samples as used in the Cofradic™ analysis. It is clear that in mouse serum samples the expression of TREML-1 is reduced during the course of sepsis, confirming the Cofradic™ results. Note that only the soluble TREML-1 is detected in serum, while both the full-length and soluble TREML-1 are detected in platelets.
Figure 8:
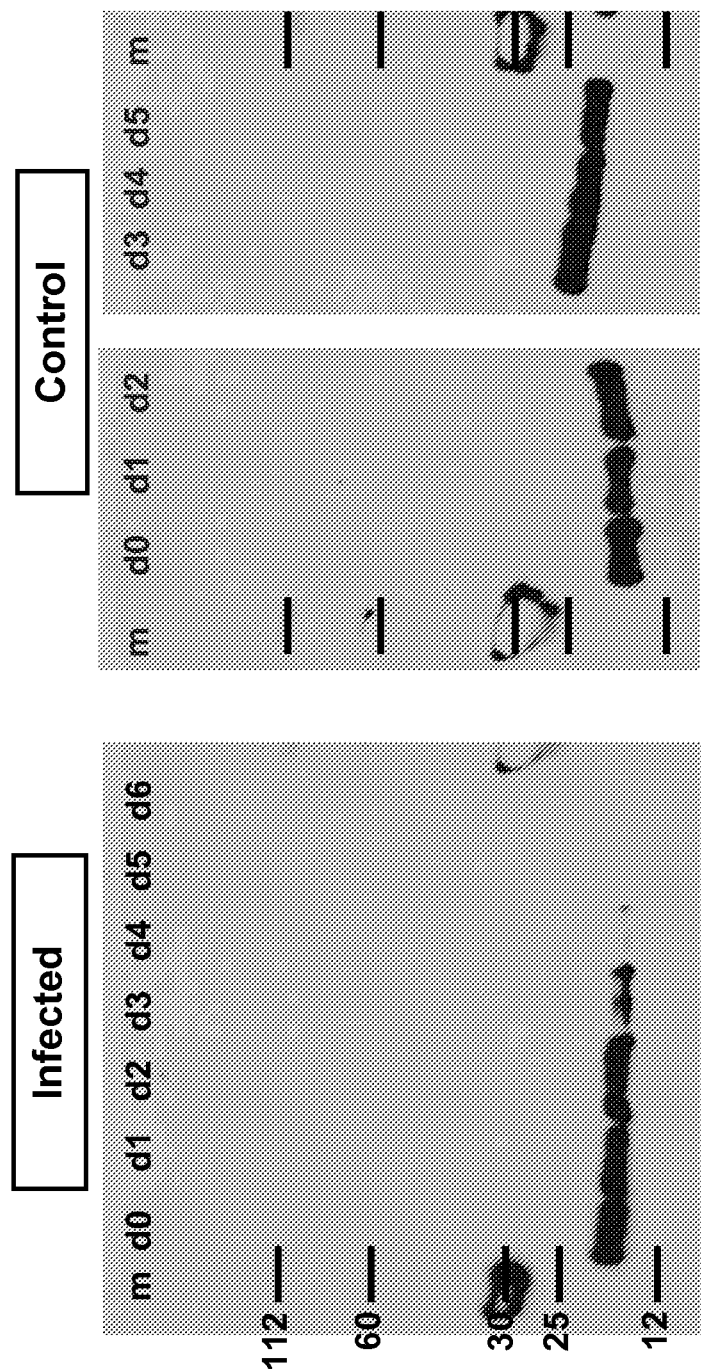
FIG. 8: Western blot analysis of an individual mouse depleted serum sample of the sepsis model (left) and of a control mouse (right) indicating no change in soluble TREML-1 expression in the control (PBS-treated) mouse and a clear reduction of TREML-1 expression in the sepsis mouse (n=2; infected with Salmonella).

Sheet 5 of 10 (Figure 5) at line 10 (approx.), Change "healthv" to --healthy--.

In the Specification

In column 3 at line 30, Change "form" to --from--.

In column 3 at line 41, Change "form" to --from--.

In column 3 at line 52, Change "form" to --from--.

In column 6 at line 4, Change "platform" to --platform.--.

In column 19 at line 27, Change "form" to --from--.

In column 19 at line 38, Change "form" to --from--.

In column 19 at line 48, Change "form" to --from--.

In column 22 at line 12, Change "sterss" to --stress--.

In the Claims

In column 24 at line 60, In Claim 1, change "(ii)" to --(iv)--.

In column 25 at line 13, In Claim 2, change "(b) the" to --(b) storing the--.

In column 26 at line 12 (approx.), In Claim 5, change "TREM 1" to --TREM-1--.

Signed and Sealed this
Twenty-third Day of September, 2014

Michelle K. Lee
*Deputy Director of the United States Patent and Trademark Office*